(12) United States Patent
Koch et al.

(10) Patent No.: US 9,585,705 B2
(45) Date of Patent: Mar. 7, 2017

(54) BONE FIXATION MEMBER SYSTEMS AND METHODS OF USE

(71) Applicant: DePuy Synthes Products, Inc., Raynham, MA (US)

(72) Inventors: Rudolf Koch, Oberdorf (CH); Stefan Knueppel, Oberdorf (CH); Raymond Schmitt, West Chester, PA (US); Arthur T. Martella, Camden, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 100 days.

(21) Appl. No.: 13/798,960

(22) Filed: Mar. 13, 2013

(65) Prior Publication Data

US 2013/0261625 A1     Oct. 3, 2013

Related U.S. Application Data

(60) Provisional application No. 61/756,758, filed on Jan. 25, 2013, provisional application No. 61/616,555, filed on Mar. 28, 2012.

(51) Int. Cl.
*A61B 17/56* (2006.01)
*A61B 17/82* (2006.01)
(Continued)

(52) U.S. Cl.
CPC ........ *A61B 17/823* (2013.01); *A61B 17/1604* (2013.01); *A61B 17/1691* (2013.01);
(Continued)

(58) Field of Classification Search
CPC .............................. A61B 17/82; A61B 17/823
See application file for complete search history.

(56) References Cited

U.S. PATENT DOCUMENTS 2,987,062 A * 6/1961 Ellison ........................... 606/74
3,570,497 A   3/1971 Lemole
(Continued)

FOREIGN PATENT DOCUMENTS

DE     3244680     6/1984
DE     3538645     5/1987
(Continued)

OTHER PUBLICATIONS

International Patent Application No. PCT/US2013/030681: International Search Report dated Jul. 5, 2013, 15 pages.

*Primary Examiner* — Nicholas Woodall
(74) *Attorney, Agent, or Firm* — Baker & Hostetler LLP

(57) ABSTRACT

A bone fixation member can be configured to secure first and second bone segments of a target bone together in a compressed approximated position. The bone fixation member can include a strap made of a first material, a locking head extending from a proximal end of the strap, and a leader portion extending from a distal end of the strap. The locking head can have a housing and a strap receiving slot that extends through the housing, slot is configured to receive a distal end of the strap. The housing can be tapered such that a distal end of the housing has a thickness that is greater than the thickness of a proximal end of the housing. The leader portion can be configured to be more flexible than the strap. The leader portion can be made of a second material that is different than the first material.

45 Claims, 15 Drawing Sheets

(51) Int. Cl.
*A61B 17/16* (2006.01)
*A61B 17/88* (2006.01)
*A61B 17/00* (2006.01)
*A61B 19/00* (2006.01)

(52) U.S. Cl.
CPC ........... *A61B 17/82* (2013.01); *A61B 17/1611* (2013.01); *A61B 17/8861* (2013.01); *A61B 17/8863* (2013.01); *A61B 17/8869* (2013.01); *A61B 19/30* (2013.01); *A61B 2017/00407* (2013.01)

(56) References Cited

U.S. PATENT DOCUMENTS

| | | | |
|---|---|---|---|
| 3,577,601 A | | 5/1971 | Mariani et al. |
| 3,835,860 A | * | 9/1974 | Garretson ................. 606/79 |
| 3,910,282 A | * | 10/1975 | Messer et al. ............... 606/226 |
| 4,037,603 A | | 7/1977 | Wendorff |
| 4,119,091 A | * | 10/1978 | Partridge ................. 606/74 |
| 4,138,770 A | | 2/1979 | Barrette et al. |
| 4,535,764 A | | 8/1985 | Ebert |
| 4,730,615 A | | 3/1988 | Sutherland et al. |
| 4,813,416 A | | 3/1989 | Pollak et al. |
| 4,901,721 A | | 2/1990 | Hakki |
| 4,955,913 A | | 9/1990 | Robinson |
| 5,146,645 A | | 9/1992 | Dirksing |
| 5,146,654 A | | 9/1992 | Caveney et al. |
| 5,193,250 A | | 3/1993 | Caveney |
| 5,318,566 A | | 6/1994 | Miller |
| 5,355,913 A | | 10/1994 | Green et al. |
| 5,356,417 A | | 10/1994 | Golds |
| 5,366,461 A | | 11/1994 | Blasnik |
| 5,383,882 A | | 1/1995 | Buess et al. |
| 5,403,346 A | | 4/1995 | Loeser |
| 5,437,685 A | | 8/1995 | Blasnik |
| 5,456,246 A | | 10/1995 | Schmieding et al. |
| 5,462,542 A | | 10/1995 | Alesi, Jr. |
| 5,549,619 A | | 8/1996 | Peters et al. |
| 5,636,412 A | | 6/1997 | Lodi et al. |
| 5,766,218 A | | 6/1998 | Arnott |
| 5,772,663 A | | 6/1998 | Whiteside et al. |
| 5,879,371 A | | 3/1999 | Gardiner et al. |
| 5,972,006 A | | 10/1999 | Sciaino, Jr. |
| 5,972,024 A | | 10/1999 | Northrup, III et al. |
| 6,049,949 A | | 4/2000 | Guthke |
| 6,489,246 B1 | | 12/2002 | Summa et al. |
| 6,589,246 B1 | | 7/2003 | Hack et al. |
| 6,613,059 B2 | | 9/2003 | Schaller et al. |
| 7,008,429 B2 | | 3/2006 | Golobek |
| 7,164,360 B2 | | 1/2007 | Schiebler |
| 7,582,089 B2 | | 9/2009 | Schiebler |
| 7,648,504 B2 | | 1/2010 | Heino et al. |
| 2003/0153947 A1 | | 8/2003 | Koseki |
| 2003/0236538 A1 | | 12/2003 | Aikens |
| 2004/0059357 A1 | | 3/2004 | Koseki |
| 2004/0068292 A1 | | 4/2004 | Koseki |
| 2005/0075667 A1 | | 4/2005 | Schaller et al. |
| 2005/0090827 A1 | | 4/2005 | Gedebou |
| 2005/0288674 A1 | | 12/2005 | Golobek |
| 2006/0149390 A1 | * | 7/2006 | Long et al. ................. 623/23.42 |
| 2006/0276809 A1 | | 12/2006 | Oliveira |
| 2007/0055258 A1 | | 3/2007 | Hansen |
| 2007/0173934 A1 | | 7/2007 | Dickinson |
| 2007/0185488 A1 | | 8/2007 | Pohjonen et al. |
| 2008/0249569 A1 | | 10/2008 | Waugh |
| 2009/0228022 A1 | | 9/2009 | McClellan |
| 2009/0306716 A1 | | 12/2009 | Beger et al. |
| 2009/0318962 A1 | | 12/2009 | Spedden et al. |
| 2010/0274289 A1 | | 10/2010 | Carls et al. |
| 2010/0292739 A1 | | 11/2010 | Schwab |
| 2010/0298829 A1 | * | 11/2010 | Schaller et al. ................. 606/74 |
| 2011/0295257 A1 | | 12/2011 | McClellan et al. |
| 2012/0041441 A1 | | 2/2012 | Bernstein et al. |
| 2012/0197256 A1 | | 8/2012 | Knueppel |
| 2012/0221060 A1 | | 8/2012 | Blain |

FOREIGN PATENT DOCUMENTS

| | | |
|---|---|---|
| DE | 4021246 | 1/1992 |
| DE | 4024334 | 2/1992 |
| DE | 4200757 | 7/1992 |
| DE | 4127550 | 2/1993 |
| DE | 4314185 | 11/1993 |
| DE | 19716504 | 12/1998 |
| DE | 19806628 | 8/1999 |
| EP | 0 009 327 | 4/1980 |
| EP | 0201905 | 11/1986 |
| EP | 0238219 | 9/1987 |
| EP | 0 299 387 | 1/1989 |
| EP | 0 512 297 | 11/1992 |
| EP | 0 597 257 | 5/1994 |
| EP | 0 608 592 | 8/1994 |
| EP | 0 780 096 | 6/1997 |
| EP | 0813846 A1 | 12/1997 |
| EP | 0 876 798 | 11/1998 |
| EP | 0 937 930 | 8/1999 |
| EP | 1 564 144 | 8/2005 |
| FR | 2677536 | 12/1992 |
| FR | 2690727 | 11/1993 |
| FR | 2702951 | 9/1994 |
| FR | 2906704 | 4/2008 |
| GB | 2266557 | 11/1993 |
| GB | 2414936 | 12/2005 |
| JP | 2004-298501 | 10/2004 |
| RU | 90673 | 1/2010 |
| RU | 2417770 | 8/2010 |
| WO | WO 88/06022 | 8/1988 |
| WO | WO 92/22041 | 12/1992 |
| WO | WO 97/16359 | 5/1997 |
| WO | WO 2005/062902 A2 | 7/2005 |
| WO | WO 2006/062419 | 6/2006 |
| WO | WO 2006/136938 | 12/2006 |
| WO | WO 2009/013397 | 1/2009 |
| WO | WO 2009/091313 | 7/2009 |
| WO | WO 2009/134424 A2 | 11/2009 |
| WO | WO 2010/041101 | 4/2010 |
| WO | WO 2010/108050 | 9/2010 |

* cited by examiner

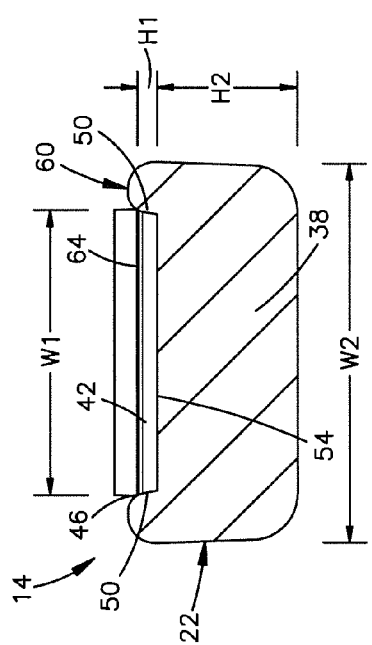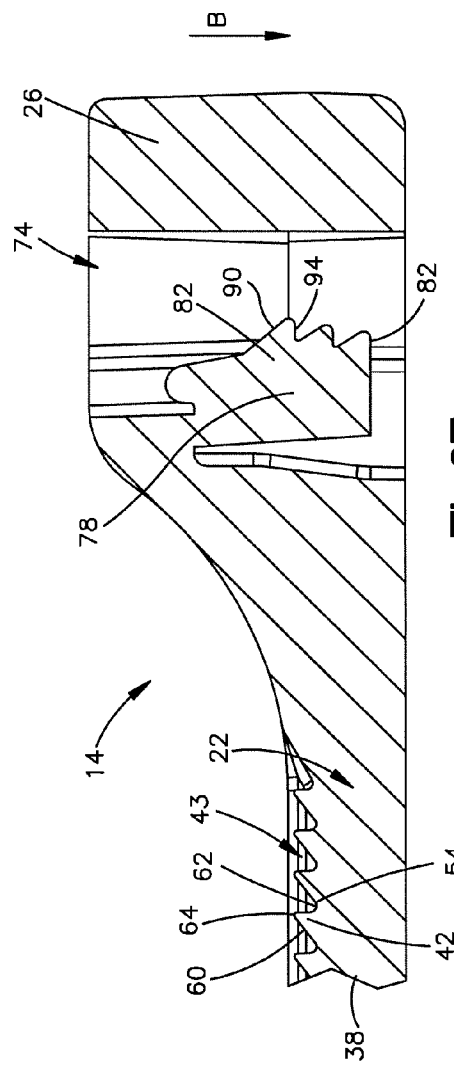

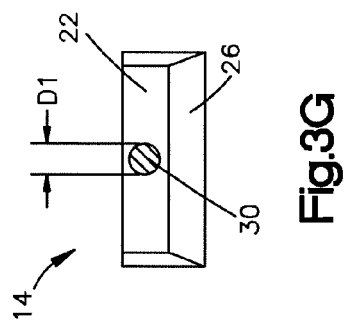
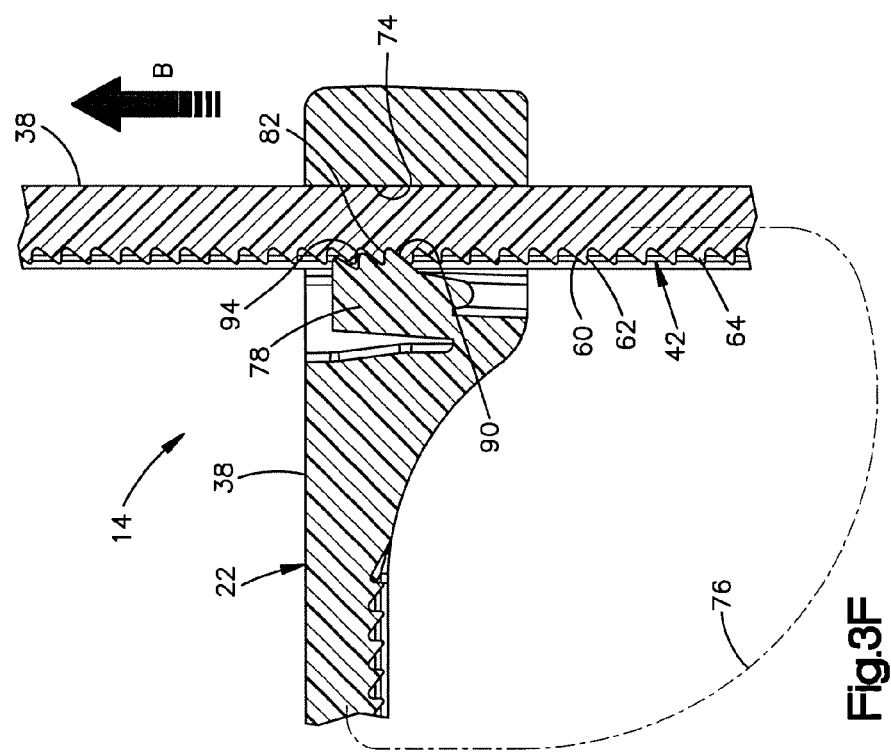

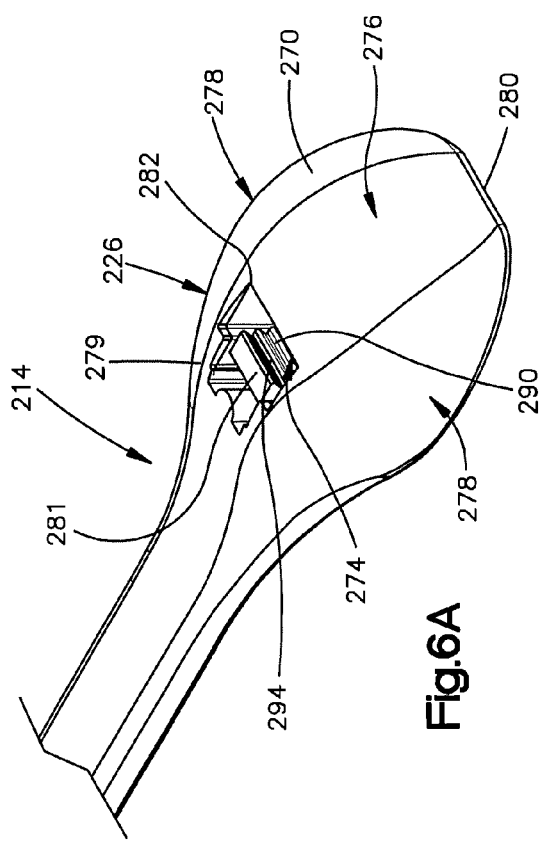
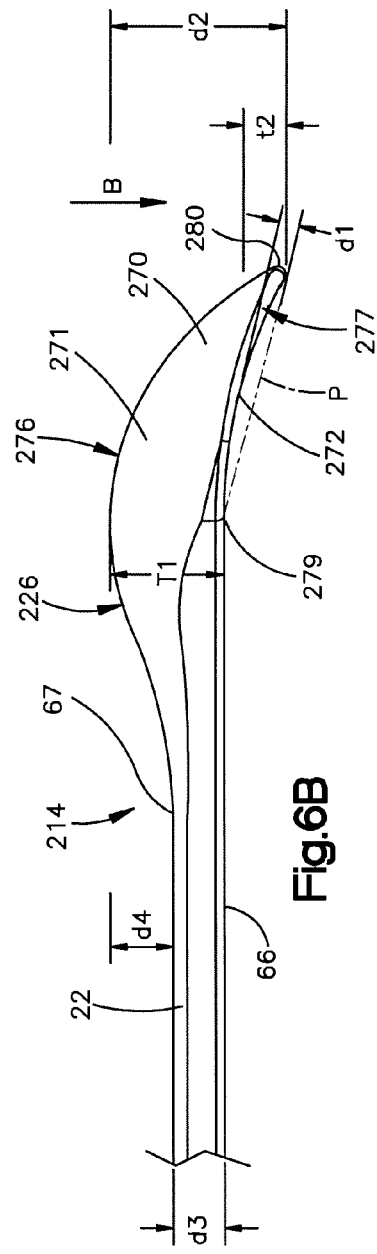

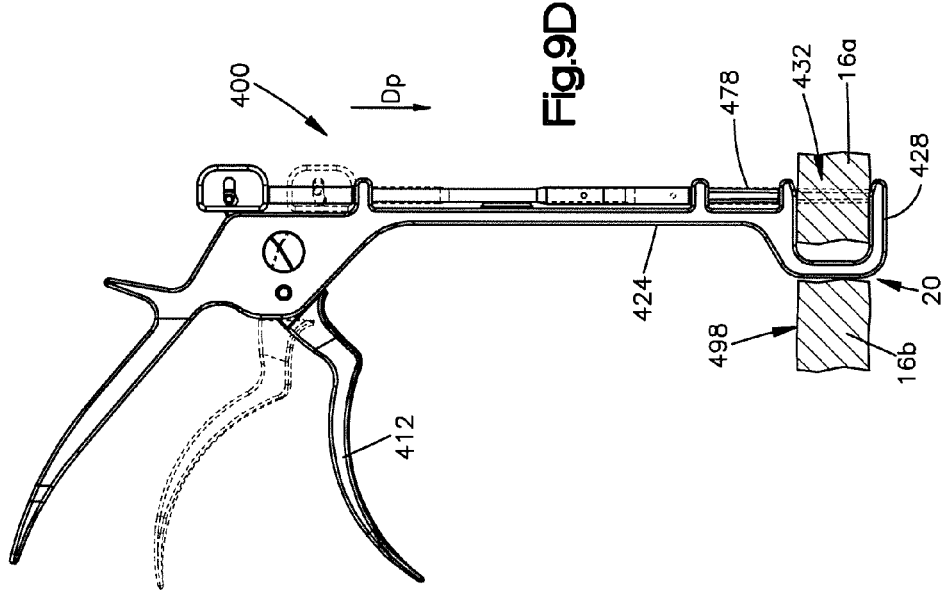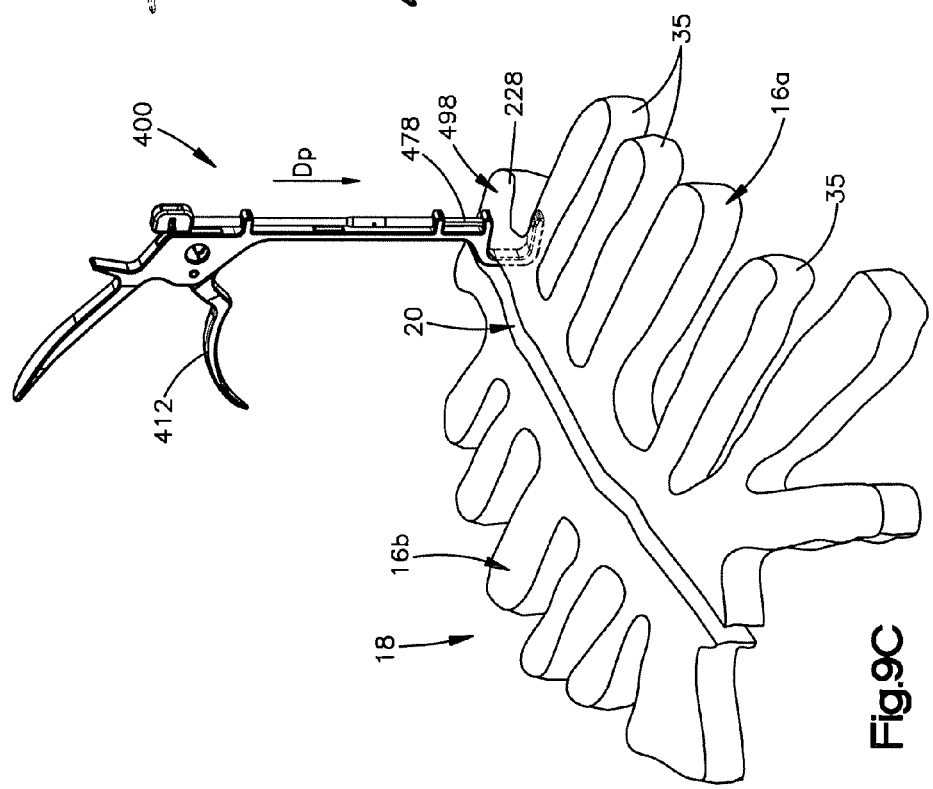

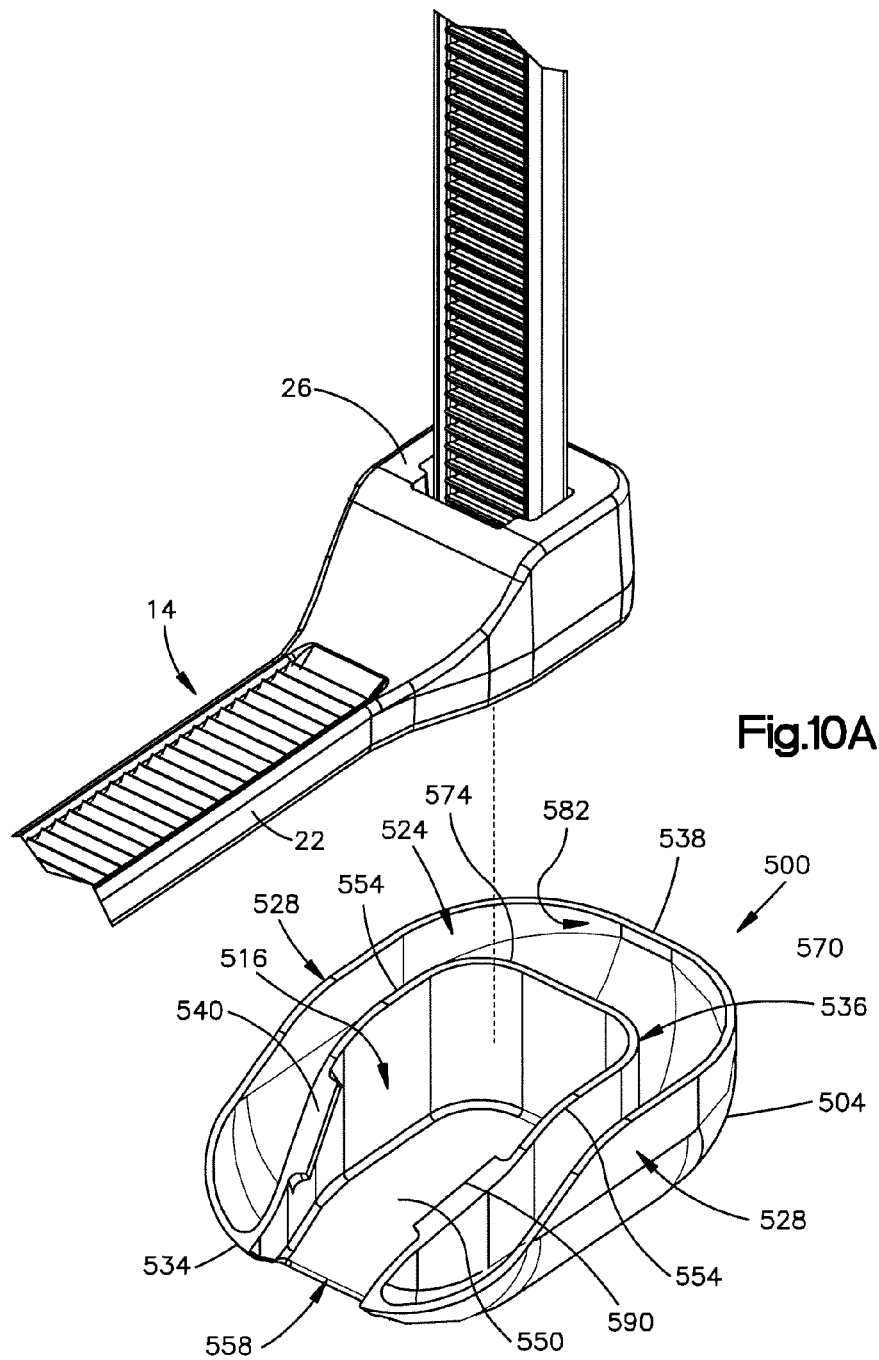

BONE FIXATION MEMBER SYSTEMS AND METHODS OF USE

CROSS REFERENCE TO RELATED APPLICATIONS

This application claims the benefit of U.S. Provisional Application Ser. No. 61,616,555, filed Mar. 28, 2012, and U.S. Provisional Application Ser. No. 61/756,758, filed Jan. 25, 2013 the contents of each of which are hereby incorporated by reference in their entireties herein.

BACKGROUND

In order to provide access to certain internal anatomy, such as the heart during an open heart procedure, midline sternotomies are typically performed. A midline sternotomy creates a cut substantially along the midline of the sternum, thereby dividing the ribcage into two halves and allowing the surgeon to move the ribcage so as to provide access to the heart. Upon completion of the open heart procedure, it is desired to approximate and compress the sternum, and rigidly maintain the sternal halves in their approximated position relative to each other so that the sterna halves are prevented from moving with respect to each other to promote bone fusion in the weeks following the surgical procedure.

During normal anatomical function, for instance during respiration, body movement, and carrying of objects, forces can be generated that act on the sternum. One conventional sternal fixation assembly includes stainless steel wires that are placed either parasternally (around the sternum) or transsternally (through the sternum bone) using a cutting needle that is attached to the wire, and subsequently twisted to tighten the wire against the sternum. However, the twisting generates tensile forces onto the wires that tend to weaken the wire, which can result in breakage both during the closure or post-operatively. Furthermore, this type of system relies on the experience of the surgeon when tightening the wires. If the wires are not tightened enough, the sternal compression can be compromised. If the wires are tightened too much, the wire can cut into or through the sternum and/or can break.

SUMMARY

In accordance with an embodiment, a bone fixation member can be configured to secure first and second bone segments of a target bone together in a compressed approximated position. The bone fixation member can include a strap that is elongate along a first direction and defines a proximal end, and a distal end spaced apart from the proximal end along the first direction. The strap can be made of at least a first material and can have a plurality of teeth. The bone fixation member can further include a locking head extending from the proximal end of the strap, a leader portion extending from a distal end of the strap, and a needle extending from a distal end of the leader portion. The locking head can have a housing, a strap receiving slot that extends through the housing, and a locking member that is connected to the housing and includes at least one complementary tooth that extends into the strap receiving slot such that when the distal end of the strap is inserted through the strap receiving slot along a second direction that is transverse to the first direction the at least one complementary tooth of the locking member engages the teeth of the strap to thereby prevent the strap from translating through the strap receiving slot along a direction that is opposite to the second direction. The housing can be tapered along the first direction such that a distal end of the housing has a thickness measured along the second direction that is greater than the thickness of a proximal end of the housing. The leader portion can be elongate along the first direction, and is configured to be more flexible than the strap. The leader portion can be made of at least a second material that is different than the first material.

Also disclosed is a method of forming holes in first and second sternal portions with a bone punch, the bone punch including a boom arm that is elongate along a punch direction, and a needle that is coupled to the boom arm and translatable relative to the boom arm along the punch direction between a first position and a second position. The method comprises the steps of positioning the bone punch such that the first sternal portion is received in a bone receiving gap defined by the boom arm and the punch direction is substantially perpendicular to an anterior surface of the first sternal portion; causing the needle to translate from the first position to the second position such that the needle passes through the first sternal portion along the punch direction to thereby form a hole in the first sternal portion; causing the needle to translate from the second position to the first position; and removing the bone punch from the first sternal portion.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 3D is an enlarged cross-sectional view of the bone fixation member shown in FIG. 3C through the line 3D-3D;

FIG. 3E is an enlarged cross-sectional view of the bone fixation member shown in FIG. 3C through the line 3E-3E;

FIG. 3F is an enlarged cross-sectional view of a portion of the bone fixation member illustrated in FIG. 3D, showing the strap inserted through the locking head so as to secure the bone fixation member about an underlying bone;

FIG. 3G is a cross-section view of a portion of the leader portion shown in FIG. 3B through the line 3G-3G;

FIG. 6A is a perspective view of a bone fixation member constructed in accordance with another embodiment, the bone fixation member having a locking head that is tapered so as to provide a lower profile and/or a smoother transition;

FIG. 6B is a side elevation view of the bone fixation member shown in FIG. 6A;

FIG. 9C is a perspective view of the bone punch shown in FIG. 9A forming a hole in the manubrium;

FIG. 9D is a partial side cross-sectional view of the bone punch shown in FIG. 9C forming the hole;

FIG. 10A is a bottom perspective exploded view of a cap constructed in accordance with an embodiment and a locking head of the bone fixation member shown in FIG. 1, the cap being configured to couple to the locking head so as to overlie the locking head and transform the locking head into a locking head that is similar to the locking head of the bone fixation member shown in FIG. 6A;

DETAILED DESCRIPTION

Figure 1:
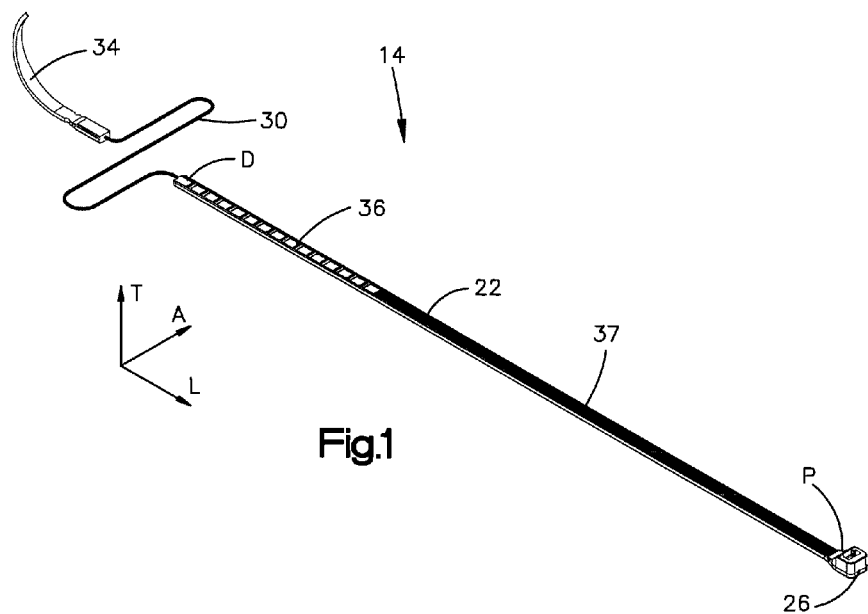
FIG. 1 is a perspective view of a bone fixation member constructed in accordance with an embodiment, the bone fixation member having a strap, a locking head extending from a proximal end of the strap, and a leader portion extending from a distal end of the strap, the leader portion being more flexible than the strap.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Figure 2:
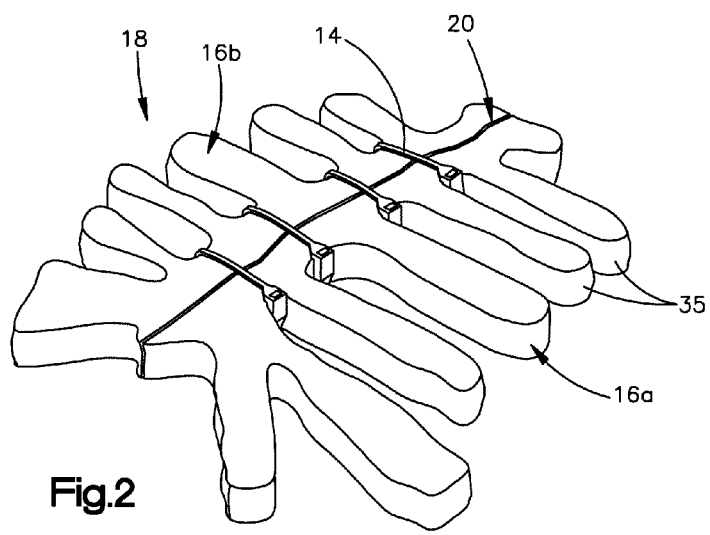
FIG. 2 is a perspective view of a plurality of the bone fixation members illustrated in FIG. 1 shown tightened about a target bone, after the leader portions and needles have been removed.

Referring to FIGS. 1 and 2, a bone fixation assembly 10 includes at least one bone fixation member 14 such as a plurality of bone fixation members that are configured to secure first and second bone segments 16a and 16b of a target bone 18, such as a sternum, that are separated at a fracture location 20 together in a compressed approximated position. As shown in FIG. 1, the bone fixation member 14 can be substantially configured as a cable tie, and extends horizontally along a longitudinal direction L and a lateral direction A, and vertically along a transverse direction T. The bone fixation member includes a flexible strap 22 that is elongate along the longitudinal direction L and defines a distal strap end D and a proximal strap end P that is spaced apart from the distal strap end D along the longitudinal direction L. The bone fixation member 14 can further include a locking head 26 that extends from the proximal strap end P along the longitudinal direction L, a flexible leader portion 30 that extends from the distal strap end D along the longitudinal direction L, and a needle 34 that extends from a distal end of the leader portion 30 along the longitudinal direction L. The leader portion 30 is configured to be more flexible than the strap 22 to permit easier implantation of the bone fixation member 14. It should be appreciated that while the longitudinal and lateral directions are described as extending horizontally and the transverse direction is described as extending vertically, that during use the plane in which the directions extend may change. For example, in use, the lateral direction may extend vertically, and the longitudinal direction and transverse direction may extend horizontally. Therefore it should be appreciated that the directional terms are for description purposes only and are not meant to be limiting.

As shown in FIG. 2, each bone fixation member 14 can be placed either parasternally or transsternally about the first and second bone segments 16a and 16b between adjacent rib bones 35. The flexible leader portions 30 provide for easier implantation of the bone fixation members 14. That is, the flexible leader portions 30 provide for greater flexibility and mobility while the bone fixation members 14 are being placed about the first and second bone segments 16a and 16b of the target bone 18. It should be appreciated, that while the bone fixation members 14 are illustrated as approximating a sternum, the bone fixation members 14 can approximate any target bone as desired, such as a long bone for example.

As shown in FIG. 1, the strap 22 can include a strap body 38 that is separated into at least a first initiation region 36 that extends from the distal strap end D toward the proximal strap end P along a portion of the length of the strap 22 (for instance, approximately ⅓ the length of the strap 22) and a second locking region 37 that extends between the first initiation region 36 and the proximal strap end P. In accordance with the illustrated embodiment, the second locking region 37 extends from the first initiation region 36 to the proximal strap end P. The first initiation region 36 can include a plurality of small protrusions that extend out from the strap body 38 and alternate with recessed regions disposed between adjacent protrusions. Alternatively, the initiation region 36 can be substantially smooth and devoid of protrusions or teeth. The second locking region 37 can include a plurality of locking teeth 42 that extend out from the strap body 38 a distance greater than the protrusions and are separated by recessed regions 43 disposed between adjacent locking teeth 42. It should be appreciated that the locking region 37 can extend along any portion up to all of the strap body 38 as desired.

As shown in FIGS. 3A-3E, The teeth 42 extend from the body 38 along a common surface and are spaced apart from each other along the longitudinal direction L. The strap 22 is made from a first flexible biocompatible material such as PEEK or PEKK. The strap 22 is configured to have a first length $L_1$ measured from the proximal strap end P to the distal strap end D that is between about 200 mm and about 300 mm, and preferably is about 270 mm. It should be appreciated, however, that the strap 22 can include any length $L_1$ as desired. Moreover, it should be appreciated that while the strap 22 includes teeth 42 that extend from a single surface, the strap 22 can be configured such that teeth 42 extend from two or more surfaces, such as two opposed surfaces for example.

As shown in FIG. 3D, the strap body 38 defines a first or bone contact surface or end 66 and a second or outer surface or end 67 spaced apart from the first end 66 along the transverse direction. The strap body 38 further defines a recess 46 that extends into the outer bone contacting surface or end 66 of the body 38 along the transverse direction T so as to be defined by opposed inner side surfaces 50 of the body 38 and an inner bottom surface 54 of the body 38. As shown in FIG. 3D, the teeth 42 extend up from the inner bottom surface 54 and toward the outer bone contacting surface 66 between the inner side surfaces 50. Each tooth 42 is elongate along the lateral direction A and is spaced from an adjacent tooth 42 along the longitudinal direction L. The teeth 42 define a beveled leading or distal edge 60 and a trailing or proximal edge 62. The leading edges 60 extend from the bottom inner surface 54 at an angle such that the leading edges 60 are configured to cam over complementary beveled leading edges of complementary locking teeth of the locking head 26. The trailing edges 62 extend from the inner bottom surface 54 along the transverse direction and are substantially perpendicular to the inner bottom surface 54 such that the trailing edges 62 are configured to engage complementary trailing edges of the locking teeth of the locking head 26. It should be appreciated, however, that the teeth 42 can have other configurations as desired. For example, the trailing edges 62 can also extend from the inner bottom surface 54 at an angle so long as the trailing edges 62 can engage complementary trailing edges of the locking teeth of the locking head 26.

The recess 46 can have a width $W_1$ that is substantially equal to the width of the teeth 42, and a height $H_1$ that is substantially equal to the height of the teeth 42. Therefore the teeth 42 can be recessed within the recess 46 so as to reduce irritation that may be caused to the target bone 18. That is, an outer edge 64 of each tooth 42 does not extend substantially beyond the outer bone contacting surface 66 of the strap body 38. Therefore, any irritation that may be caused by the teeth 42 can be reduced. It should be appreciated, however, that in some embodiments a portion of the teeth 42 may extend beyond the outer bone contacting surface 66 of the strap body 38. It should also be appreciated that the width $W_1$ and the height $H_1$ of the recess 46 can vary as desired.

As shown in FIGS. 3D and 3E, the strap 22 can have an overall width $W_2$ that extends along the lateral direction A and a height $H_2$ that extends along the transverse direction T and is measured between adjacent teeth 42. The width $W_2$ and the height $H_2$ can be configured such that a cross-section of the strap 22 taken between adjacent teeth 42 has an area that is between about 4.0 mm² and about 8.0 mm². It should be appreciated, however, that the strap 22 can have any cross-sectional area as desired, so long as the strap 22 is flexible enough to be placed about the target bone 18 without breaking. The width $W_2$ of the strap 22 can also vary depending on the target bone 18 that the bone fixation member 14 is to be placed. For example, space between adjacent ribs may vary thereby limiting the width $W_2$. That is, if the space between adjacent ribs is narrow, the width $W_2$ of the strap 22 will also have to be narrow so that the bone fixation member 14 can be placed about the bone. Moreover, by providing the strap 22 or at least the strap body 38 with a greater width $W_2$, the outer bone contacting surface 66 can be increased so as to reduce complications such as sternal non-union or sternal infection sometimes caused when using wires. Therefore, a greater width $W_2$ provides a greater bone contacting surface 66 for the bone fixation member 14 so as to further reduce any complications typically associated with bone fixation.

Figure 3A:
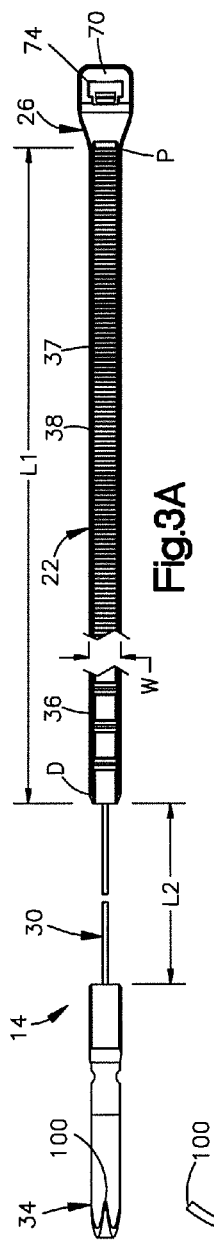
FIG. 3A is a top plan view of the bone fixation member shown in FIG. 1.
Figure 3B:
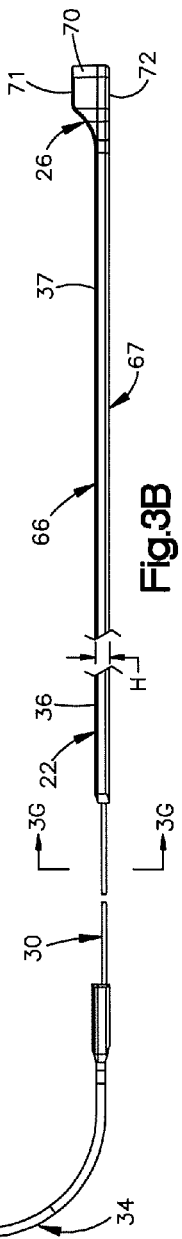
FIG. 3B is a side elevation view of the bone fixation member shown in FIG. 3A.
Figure 3C:
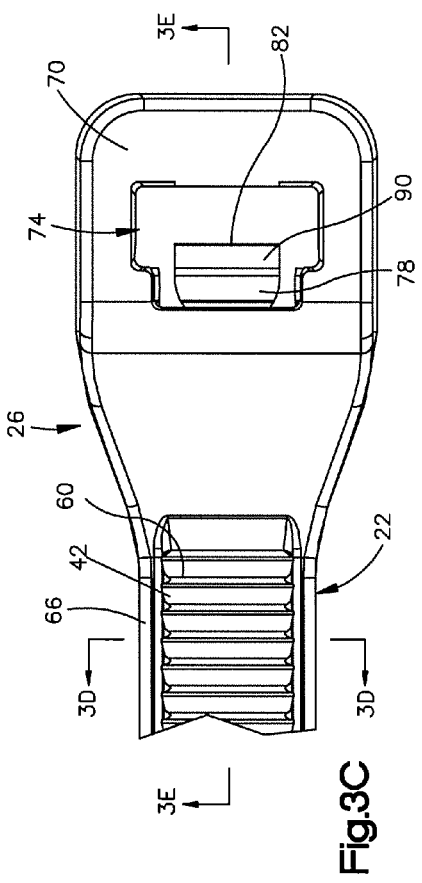
FIG. 3C is an enlarged top plan view of the locking head of the bone fixation member shown in FIG. 3A.

Now in reference to FIGS. 3C, 3E and 3F, the locking head 26 is configured to receive the distal strap end D of the strap 22. As shown, the locking head 26 includes a housing 70 that defines a first head end 72 and a second head end 71 spaced from the first head end 72 along the transverse direction. The locking head 26 further includes a strap receiving slot 74 that extends through the housing 70 from the second head end 71 to the first head end 72 along a second direction. The slot 74 can extend along the second direction which can be along the transverse direction T or along a direction having a directional component that extends along the transverse direction T. Therefore, the slot 74 can extend through the housing 70 at an angle relative to the longitudinal direction L. The strap receiving slot 74 is configured to receive the distal strap end D of the strap 22 such that the strap 22 is configured to translate through the slot 74 uni-directionally along an insertion direction B which can be the second direction so as to define a loop 76 about the target bone 18. Therefore, the strap 22 can translate through the slot 74 along the insertion direction, but not along a direction opposite the insertion direction.

The locking head 26 further includes a toothed locking member 78 that is connected to the housing 70 and has at least one, such as three complementary teeth 82 that extend into the strap receiving slot 74. The locking member 78 is configured to elastically flex as the strap 22 is passed through the slot 74 so as to allow the strap 22 to incrementally pass through the slot along the insertion direction. The locking member 78 has a width $W_3$ that is substantially equal to or less than the width $W_1$ of the recess 46. Therefore, as the strap 22 is passed through the slot 74 the locking member 78 will extend into the recess 46 such that the locking teeth 82 of the locking member 78 can engage the locking teeth 42 of the strap 22.

As shown in FIG. 3E, the locking teeth 82 define a beveled leading edge 90 that is configured to cam over the complementary beveled leading edges 60 of the locking teeth 42 when the strap 22 is translated through the slot 74 along the insertion direction. The locking teeth 82 further define trailing edges 94 that are sloped less than the beveled leading edges 90, such that the trailing edges 94 engage the trailing edges 62 of the teeth 42 to prevent the strap 22 from translating through the slot 74 along a direction opposite the insertion direction B to thereby prevent the loop 76 from increasing. Therefore, the locking head 26 is configured to allow the strap 22 to translate uni-directionally through the slot 74 along the insertion direction B so as to reduce the size of the loop 76 about the first and second segments 16a and 16b of the target bone 18 but not along the direction opposite the insertion direction B so as to increase the size of the loop 76.

The strap 22 and locking head 26 are integrally formed and may be molded as a monolithic structure. The strap 22 as molded is configured to be flexible and strong enough so as to avoid the risk of breakage during inter-operative excessive bending or buckling. The strap 22 and locking head 26 can be molded out of PEEK or PEKK. To form the strap 22 and locking head 26, a hot polymer melt can be injected into a mold having a cavity that defines the strap 22 and locking head 26 part. Once injected, the melt can be subsequently cooled to thereby form the strap 22 and locking head 26 part. It should be appreciated, however, that strap 22 and locking head 26 may be made from other materials as desired, so long as the strap 22 is flexible.

When the strap 22 and locking head 26 are made of PEEK, the molding process can be configured to prevent the PEEK polymer from crystallization during the cooling process. This can be accomplished by quenching the hot polymer melt by injection molding the PEEK polymer melt into a cool mold. For example, the mold temperature can be between about 10° C. and about 120° C., and preferably between about 25° C. and 80° C. The cool molds can reduce the crystallization of the PEEK polymer thereby increasing the strength and flexibility of the part.

When the strap 22 and locking head 26 are made of PEKK, the parts may be molded without quenching. PEKK exhibits extremely small crystallization rates, and during injection molding, the parts cool down and solidify prior to crystallization. The resulting parts may have an increased strength and won't break when being excessively bent or buckled. Because the strap 22 and locking head 26 can be made without quenching, the length of the strap 22 and the width of the strap 22 won't be limited, which may be the case when the strap 22 and locking head 26 are quenched after being injected into the mold.

Now referring to FIGS. 3A, 3B, and 3G, the leader portion 30 extends from the distal strap end D of the strap 22 and is elongate along the first direction L. The leader portion 30 is made of a second material that is different than the first material that the strap 22 is made from. For example, the leader portion 30 can be made from a metal such as stainless steel. A stainless steel leader portion 30 may allow the leader portion 30 to be bent or twisted, rendering it easy to handle. It should be appreciated, however, that the leader portion 30 can be made from other materials, such as non-PEEK or non-PEKK materials, for example a suture material. As shown in FIG. 3A, the leader portion can define an overall second length $L_2$ measured along the first direction that is at least 25% of the length of the strap 22 (i.e. the first length $L_1$), and preferably at least 33% of the first length $L_1$. For example, the leader portion 30 can have a length $L_2$ that is between about 100 mm and about 300 mm. It should be appreciated, however, that the leader portion 30 can have any length as desired. For example, the leader portion 30 can have a length that is equal to the length $L_1$ of the strap 22.

As shown in FIG. 3G, the leader portion 30 can be a cable having a cross-sectional dimension, such as a diameter $D_1$ that is between about 0.6 mm and about 1.5 mm. The entire length or at least a majority of the length of the leader portion 30 can have the diameter $D_1$. Therefore, the entire length or at least a majority of the length of the leader portion 30 can have a cross-sectional area that is between about 0.5 mm$^2$ and about 0.8 mm$^2$. Therefore, the bone fixation member 14 can have a leader portion cross-sectional area to strap cross-sectional area ratio that is between about 0.063 and about 0.13. It should be appreciated, however, that the bone fixation member 14 can have cross-sectional areas such that the ratio falls outside of the stated range, as desired. The material choice, the cross-sectional area, the shape, and the length of the leader portion 30 can all provide for greater flexibility as compared to the strap 22, so as to allow the bone fixation member 14 to be more easily implanted.

The proximal end of the leader portion 30 may be coupled to the distal strap end D of the strap 22 either after or during the molding of the strap 22. For example, the proximal end of the leader portion 30 may be overmolded onto the distal strap end D of the strap 22 when the strap 22 is being formed in the mold. Alternatively, the distal strap end D of the strap 22 can include a metal insert and the proximal end of the leader portion 30 can be coupled to the metal insert by a weld. It should be appreciated, however, that the leader portion 30 can be coupled to the strap 22 by other connections, for example by a knot.

As shown in FIGS. 3A and 3B, the needle 34 extends from a distal end of the leader portion 30. The needle 34 can be made of stainless steel. Therefore, the needle 34 and the leader portion 30 can be integrally formed (i.e. monolithic) or the needle 34 can be coupled to the leader portion 30 via a weld, knot, or other connection. As shown, the needle 34 initially extends distally, then curves up and around such that a tip 100 of the needle 34 extends at least partially toward the proximal end P of the strap 22. The curved needle 34 allows the needle 34 and leader portion 30 to be more easily passed through the target bone 18 and the strap receiving slot 74 of the locking head 26. It should be appreciated, however, that the needle 34 can have other configurations, as desired. For example, the needle 34 can be straight, or made from a material other than stainless steel.

During operation, the strap 22 is placed about the first and second bone segments 16a and 16b of the target bone 18, and the needle 34 is inserted through the slot 74 and pulled through the slot 74 so as to cause the strap 22 to subsequently translate through the slot 74. The needle 34 and leader portion 30 can be removed from the strap 22, and the strap 22 can then be further pulled, for instance manually, through the slot 74. As the strap 22 is translated through the slot 74 along the insertion direction B, the small protrusions of the initiation region 36 of the strap 22 can slide through the slot 74 without engaging the locking teeth 82 of the locking head 26. As the locking region 37 of the strap 22 is translated through the slot 74 of the locking head 26 along the insertion direction, the locking teeth 42 and 82 can engage to prevent the tension that is induced in the strap 22 from causing the strap 22 to back out of the slot 74 along a direction opposite the insertion direction B. For instance, as the strap 22 translates through the locking head 26 along the insertion direction, the size of the loop 76 about the target bone 18 decreases until tactile feedback indicates that tension has been induced in the strap 22.

Figure 4:
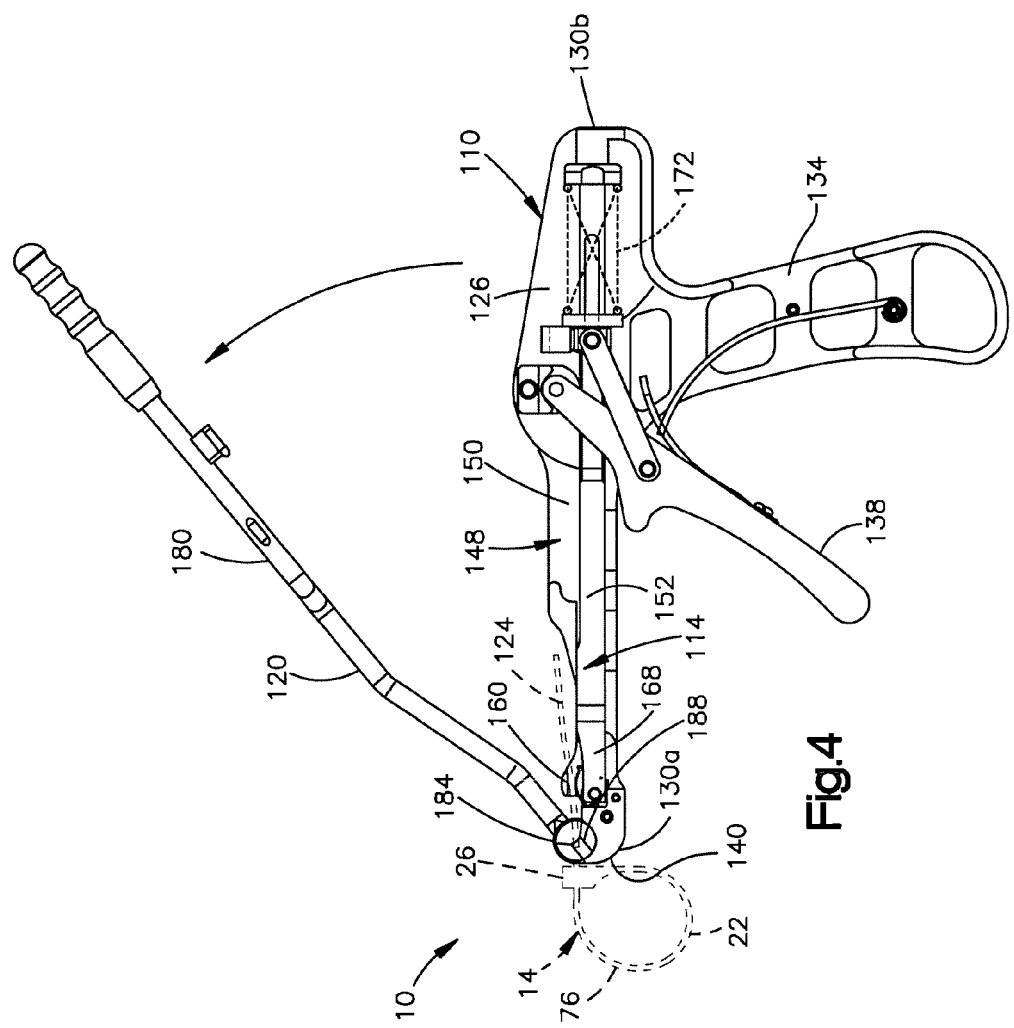
FIG. 4 is a perspective view of a bone fixation instrument constructed in accordance with an embodiment, the bone fixation instrument configured to tighten and subsequently cut the strap of the bone fixation member shown in FIG. 1.

Now in reference to FIG. 4, the bone fixation assembly 10 can further include a fixation instrument 110 that is configured to further tighten the bone fixation members 14 about the target bone 18. The bone fixation instrument 110 can be similar to the bone fixation instrument disclosed in U.S. patent application Ser. No. 13/019,907, filed Feb. 2, 2011 and assigned to Synthes USA, LLC, the contents of which are hereby incorporated by reference in their entirety herein. As shown in FIG. 4, the fixation instrument 110 can include a tension assembly 114 that is configured to secure the fixation instrument 110 to the strap 22, and is further configured to further pull the strap 22 through the locking head 26 thereby further inducing tension in the strap 22 until the strap 22 has securely compressed the first and second bone segments 16a and 16b of the target bone 18 together at the fracture location. As illustrated in FIG. 4, the fixation instrument 110 further includes a cutter assembly 120 that is configured to cut a free end 124 of the strap 22 that has passed through the locking head 26 once a desired tension has been induced in the strap 22 about the first and second segments 16a and 16b of the target bone 18. For instance, the desired tension can be within a range defined by and between a lower end that can be approximately 50 Newtons or approximately 80 Newtons, and an upper end that can be approximately 150-160 Newtons or 200 Newtons. It should be appreciated that the desired tension can depend on the bone quality and the preference of the surgeon, and can for instance be any tension as desired that reliably secures the target bone 18 without over tightening the strap 22. It should further be appreciated, that the bone fixation assembly 10 can include other bone fixation instruments that are configured to provide tension to the bone fixation members 14. Moreover it should be appreciated that the bone fixation assembly 10 can be void of a bone fixation instrument and tension can be applied manually by an individual.

With continued reference to FIG. 4, the fixation instrument 110 includes a body 126 that defines a front end 130a and an opposed rear end 130b, and a handle 134 that is supported by the body 126, and extends down from the body 126 at an angle. The fixation instrument 110 further includes a trigger 138 that extends down from the body 126 at a location spaced forward from the handle 134, and a nose 140 disposed at the front end 130a of the body 126. The handle 134, the trigger 138, and the nose 140 can be discreetly attached to the body 126 or integral with the body 126 as desired. The body 126 can include an outer housing 148 that includes a pair of housing members 150 that are laterally opposed and define respective outer sides 152 and can be joined together via fasteners such as screws so as to support the various internal components of the fixation instrument 110.

For instance, the housing 148 can support the tension assembly 114 that is configured to tighten the bone fixation member 14, thereby inducing tension in the bone fixation member 14, and can further support the cutter assembly 120 that is configured to remove a free end 124 of the bone fixation member 14 once the tension assembly 114 has induced a desired level of tension in the bone fixation member 14. The tension assembly 114 includes a grip 160 that is movable between a disengaged position, whereby the grip 160 is configured to loosely receive the strap 22, such as the portion of the strap that has passed through the locking head 26, and an engaged position whereby the grip 160 is configured to be secured to the received strap 22. The tension assembly 114 further includes a traveler 168 that is operably coupled to the grip 160 and extends rearward from the grip 160, such that rearward movement of the traveler 168 causes the grip 160 to move rearward in the secured configuration, thereby inducing tension in the strap 22.

The tension assembly 114 can further include a tension limiter 172 that is connected between the trigger 138 and the traveler 168. The tension limiter 172 can be configured to apply a force that is greater than, but corresponds to, the tension in the loop 76 about the target bone 18. Thus, the maximum force applied by the tension limiter 172 can correspond to the maximum desired tension in the loop 76, it being appreciated that once the teeth 42 and 82 ride over and past each other, the tension in the loop 76 can decrease somewhat as the teeth 42 and 82 interlock. In accordance with one embodiment, the tension limiter 172 can apply a maximum force as desired that corresponds to a desired maximum tension in the loop 76 about the target bone 18. As a result, once the desired maximum tension in the loop 76 has been induced about the target bone 18, the force applied by the tension limiter 172 when the trigger 138 is fully actuated is insufficient to cause the teeth 42 and 82 to ride past each other and further tighten the loop 76. Accordingly, once the maximum tension in the loop 76 has been induced about the target bone 18, the force applied by the tension limiter 172 will be insufficient to cause the traveler 168 to translate rearward a sufficient distance that further tightens the loop 76 about the target bone 18.

The cutter assembly 120 is configured to cut the free end 124 of the strap 22 after the strap 22 has been tightened. The cutter assembly 120 includes a cutter arm 180 movably supported by the body 126 and a cutter blade 184 that is carried by the cutter arm 180. The cutter arm 180 is movable from a seated disengaged position whereby the cutter blade 184 is spaced from the free end 124 of the strap 22 that is received in the grip 160 to an engaged position whereby the cutter blade 184 cooperates with a complementary cutter blade 188 of the nose 140 so as to cut the free end 124 of the strap 22.

Figure 5A:
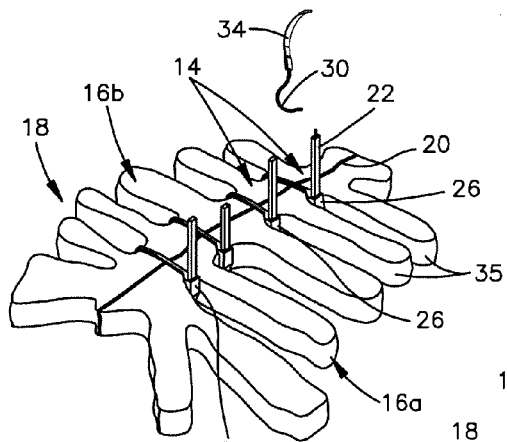
FIG. 5A is a perspective view of the bone fixation members placed about the target bone after the leader portions and needles have been removed from the straps.

In operation, and in reference to FIGS. 4, and 5A-5C, the bone fixation members 14 may be placed about the bone segments 16a and 16b of the sternum between adjacent ribs 35. For each bone fixation member 14, the needle 34 and leader portion 30 can be passed through the slot 74 and pulled through the slot 74 so as to cause the strap 22 to subsequently translate through the slot 74. As shown in FIG. 5A, the needle 34 and leader portion 30 can be removed from the strap 22, and the strap 22 can then be further pulled, for instance manually, through the slot 74. As the strap 22 is translated through the slot 74 of the locking head 26 the locking teeth 42 and 82 can engage to prevent the tension that is induced in the strap 22 from causing the strap 22 to back out of the slot 74.

Figure 5B:
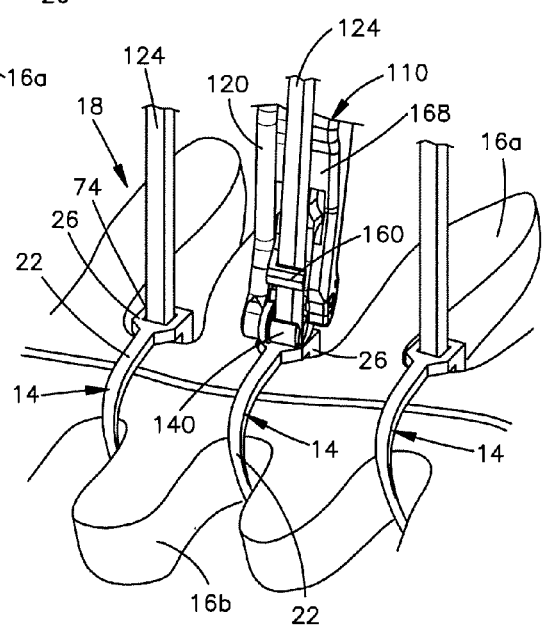
FIG. 5B is a perspective view of the bone fixation instrument illustrated in FIG. 4 operatively coupled to and tightening one of a plurality of the bone fixation members illustrated in FIG. 5A.

As shown in FIG. 5B, the free end 124 of the strap 22, that is left after the needle 34 and leader portion 30 have been removed, can then be received in the grip 160 of the fixation instrument 110. As shown, the nose 140 is placed against the housing 70 of the locking head 26, and the trigger 138 is moved from a first initial position to a second grip position that causes the grip 160 to iterate from the disengaged position to the engaged position, and is further moved from the second grip position to a third tension position that causes the traveler 168 to move rearward, thereby inducing tension in the strap 22 when the tension in the strap 22 is less than a select tension, which can be a desired maximum tension as determined by the tension limiter 172. When the tension in the strap 22 reaches the maximum tension, the tension limiter 172 prevents the traveler 168 from moving rearward when the trigger 138 is moved to the tension position.

Figure 5C:
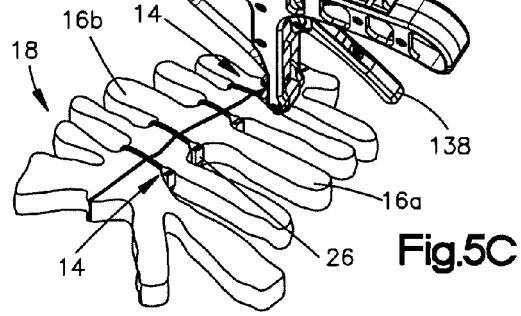
FIG. 5C is a perspective view of the bone fixation instrument cutting one of the tightened bone fixation members illustrated in FIG. 5B.

As shown in FIG. 5C, once the strap 22 has reached a maximum desired tension, the cutter assembly 120 can be actuated to remove the free end 124 of the bone fixation member 14. To do so, the cutter arm 180 is pivoted such that the cutter arm 180 moves away from the body 126. As the cutter arm 180 is pivoted the cutter blade 184 that is carried by the cutter arm 180 moves toward the complementary cutter blade 188 of the nose 140 so as to pinch and then subsequently cut the free end 124 of the strap 22. The free end 124 may then be removed, leaving the remainder of the bone fixation member 14 behind to hold the bone segments 16a and 16b together. As shown in FIG. 5C, the bone fixation members 14 are oriented with respect to the sternum such that the locking heads 26 are positioned within the gap between adjacent rib bones 35. Therefore, the amount of the locking head 26 that can jut out into the soft tissue can be reduced, thereby reducing irritation that may be caused to the surrounding soft tissue by the locking head 26.

Figure 7A:
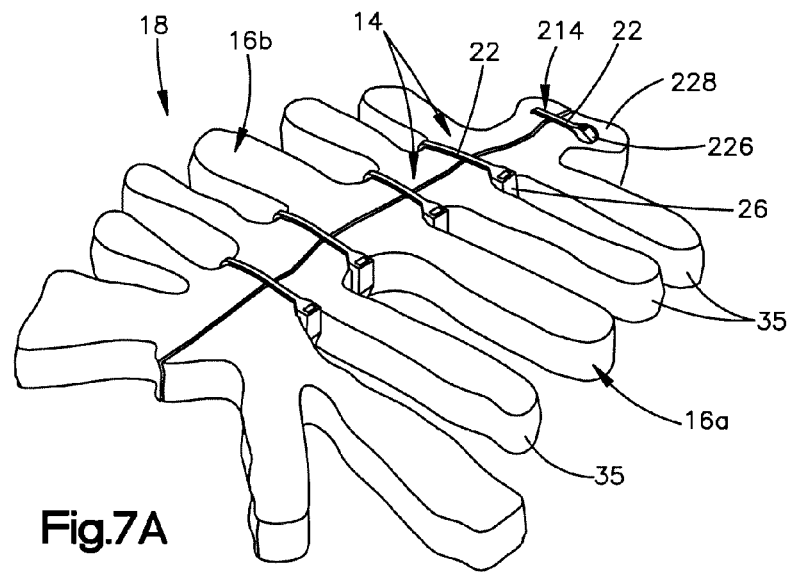
FIG. 7A is a perspective view of the bone fixation member illustrated in FIG. 6A shown tightened about the manubrium.

Now in reference to FIGS. 6A, 6B, and 7A a bone fixation member 214 can be configured to have a tapered locking head 226. The tapered locking head 226 provides a lower profile and/or a smoother transition so as to further reduce irritation that may be caused to the surrounding soft tissue by the locking head 226. The bone fixation member 214 can be placed either parasternally or transsternally about the first and second bone segments 16a and 16b of the sternum proximate to the manubrium 228 for example as show in FIGS. 7B and 7C. Therefore it can be said that the bone fixation member 214 can be configured approximate first and second manubrium portions 228. It should be appreciated, however, that the bone fixation member 214 can be placed about any location of the sternum as desired or about another bone as desired. The bone fixation member 214 is substantially similar to the bone fixation member 14 and includes like features unless otherwise described. Therefore, it should be appreciated that the bone fixation member 214 can include a strap 22, a leader portion 30, and a needle 34 as described with respect to the bone fixation member 14 shown in FIGS. 3A-3G.

As shown in FIGS. 6A and 6B, the locking head 226 is configured to receive a distal strap end of the strap 22. As shown, the locking head 226 includes a housing 270 that defines a first or upper end 271 and a second or lower end 272 that is spaced from the first end 271 along the transverse direction. The locking head further includes a strap receiving slot 274 that extends through the housing 270 from the upper end 271 to the lower end 272 along a second direction. The slot 274 can extend along the second direction which can be along the transverse direction T or a direction having a directional component that extends along the transverse direction T. The strap receiving slot 274 is configured to receive the distal strap end D of the strap 22 such that the strap 22 is configured to translate through the slot 274 uni-directionally along an insertion direction B which can be the second direction so as to define a loop about the target bone 18.

The first end 271 of the housing 270 defines an upper surface 276, and the second end 272 of the housing 270 defines a lower surface 277. The first housing further defines two opposed side surfaces 278 that merge into the upper and lower surfaces 276 and 277. As shown in FIG. 6B, the housing 270 is tapered along the longitudinal direction L and includes a distal head end 279 and a proximal head end 280 spaced from the distal head end 279 along the longitudinal direction L. The housing 270 can be tapered such that the distal head end 279 of the housing 270 has a first height $T_1$ measured along the transverse direction T and the proximal head end 280 has a second height $T_2$ measured along the transverse direction T. The first height $T_1$ can be about 4.5 mm. The height or thickness of the housing 270 tapers as the housing extends proximally. Therefore, the second height $T_2$ is less than the first height $T_1$. The thicker distal head end 279 provides stability and rigidity to the locking head 226 while the thinner proximal head end 280 provides a lower profile and/or a smoother transition for the locking head 226 when the locking head 226 has been placed about the target bone. It should be appreciated, however, that the housing 270 can have any first height $T_1$ and any second height $T_2$ as desired.

The upper surface 276 is convex along the longitudinal direction L and the lower surface 277 is concave along the longitudinal direction L. The convex upper surface 276 and the concave lower surface 277 converge toward each other as they extend from the distal head end 279 toward the proximal head end 280 along the longitudinal direction L. The convex upper surface 276 provides a smooth outer surface for the locking head 226 to reduce irritation to the surrounding tissue. The concave lower surface 277 provides clearance for the strap 22 when the strap 22 is translated through the strap receiving slot 274. The lower surface 277 defines a shallow curve such that a maximum distance $d_1$ measured between the lower surface 277 and a plane P defined by the locking head 226 that extends linearly through a distal end of the lower surface 277 to a proximal end of the lower surface 277 is between about 3 mm and about 5 mm. It should be appreciated, however, that the lower surface can have a deeper or shallower curve as desired, or even be void of a curve as desired.

As shown in FIG. 6B, the upper surface 276 is curved such that the slope of the upper surface 276 increases as the upper surface 276 extends from the distal end 279 toward the proximal end 280. The lower surface 277 is also curved such that the slope of the lower surface 277 increases but at a rate that is substantially less than the rate at which the slope of the upper surface 276 increases. In particular, the rate at which the slope of the upper surface 276 increases is greater than the rate at which the slope of the lower surface 277 increases for a majority of a length of the upper surface 276. The difference in rates at which the slopes increase allows the upper and lower surfaces 276 and 277 to converge more quickly so as to provide a lower profile and/or a smoother transition.

With continued reference to FIG. 6B, the upper surface 276 of the locking head 226 merges into the upper surface or end 67 of the strap 22 such that a small portion of the upper surface 276 protrudes above the upper surface 67. For example, a maximum distance $D_4$ measured between the upper surface 67 of the strap 22 and an upper most portion of the first end 271 of the locking head 226 along the insertion direction B can be less than about 2.4 mm. Moreover, a maximum distance $d_2$ measured along the second direction between the upper most portion of the first end 271 of the locking head 226 and a lower most portion of the second end 272 is no more than 1.5 times a maximum distance or height $d_3$ measured between the upper surface or end 67 and the bone contacting surface or end 66 of the strap 22 along the second direction. Therefore, the geometry of the locking head 226 provides a lower profile and/or a smoother transition for the locking head 226 when in use. It should be appreciated, that in some embodiments no portion of the upper surface 276 protrudes above the upper surface 67.

In the illustrated embodiment, the locking head 226 is constructed as a single monolithic unit. It should be appreciated, however, that the locking head 226 can include a cap that is placed over the housing 270 such that the cap at least partially defines the first end 271. Therefore, the cap can define the convex upper surface 276 of the locking head 226.

Referring back to FIG. 6A, the side surfaces 278 are convex and converge toward each other as they extend from a midline of the housing 270 toward the distal head end 279 and toward the proximal head end 280 along the longitudinal direction L. Therefore, the housing 270 generally has an oval shape as appeared from above the locking head 226. The curved side surfaces 278 can reduce irritation that may be caused to the surrounding tissue by the locking head 226.

The locking head 226 further includes a toothed locking member 281 that is connected to the housing 270 and has at least one, such as three complementary teeth 282 that extend into the strap receiving slot 274. The locking member 281 is configured to flex as the strap 22 is passed through the slot 274 so as to allow the strap 22 to incrementally pass through the slot along the insertion direction. The locking teeth 282 define a beveled leading edge 290 that is configured to cam over the complementary beveled leading edges 60 of the locking teeth 42 when the strap 22 is translated through the slot 274 along the insertion direction B. The locking teeth 282 further define trailing edges 294 that are sloped less than the beveled leading edges 290, such that the trailing edges 294 engage the trailing edges 62 of the teeth 42 to prevent the strap 22 from translating through the slot 274 along a direction opposite the insertion direction B to thereby prevent the loop from increasing. Therefore, the locking head 226 is configured to allow the strap 22 to translate uni-directionally through the slot 274 along the insertion direction B so as to reduce the size of the loop about the first and second segments 16a and 16b of the target bone 18.

Figure 7B:
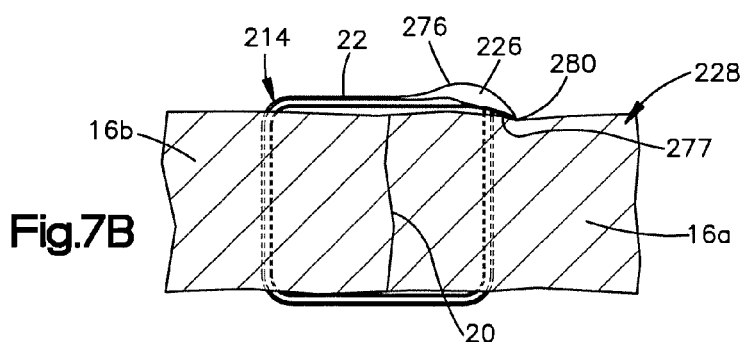
FIG. 7B is a cross-sectional side view of the bone fixation member illustrated in FIG. 6A placed transsternally about the sternum proximate to the manubrium with the locking head positioned on top of the manubrium.
Figure 7C:
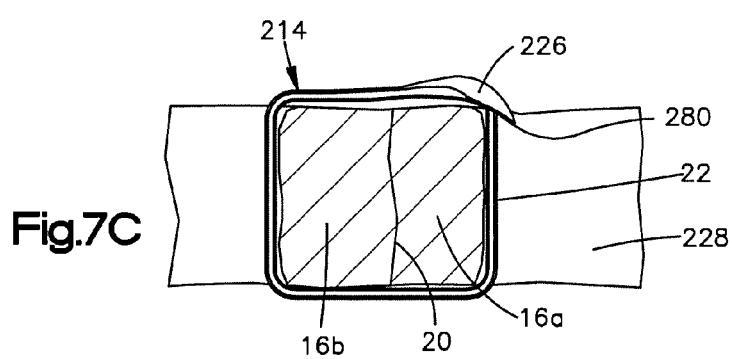
FIG. 7C is a cross-sectional side view of the bone fixation member illustrated in FIG. 6A placed parasternally about the sternum proximate to the manubrium.

As shown in FIGS. 7A and 7B, the bone fixation member 214 is configured to be placed about the bone segments 16a and 16b proximate to the manubrium 228. As shown in FIG. 7B, the bone fixation member 214 can be placed transsternally about the bone segments 16a and 16b proximate to the manubrium such that the locking head 226 is positioned on the manubrium 228. That is, the needle 34 can be translated transversely through the second bone segment 16b along a first direction then transversely through the first bone segment 16a along a direction substantially opposite to the first direction until the locking head 226 is proximate to the manubrium portion 228 of the first bone segment 16a. Therefore, it can be said that the bone fixation member 214 is configured to approximate first and second manubrium portions. It should be appreciated that the bone fixation member 214 can be passed through either the first bone segment 16a or second bone segment 16b first and is not limited to the configuration shown in FIG. 7B. The needle 34 and leader portion 30 can then be translated through the slot 274 of the locking head 226 until the strap 22 engages the locking head 226 and approximates the bone segments 16a and 16b. It should be appreciated, however, that the bone fixation member 214 may also be placed parasternally as shown in FIG. 7C. The lower profiled locking head 226 can reduce the amount of irritation that may be caused by the locking head 226 to the surrounding tissue. For example, if the bone fixation member 14 were to be placed about the bone segments 16a and 16b proximate to the manubrium 228, the locking head 26 which does not have as low of a profile and has sharper edges as compared to the locking head 226 may jut out and irritate the surrounding tissue. It should be appreciated, however, that the bone fixation member 14 can be placed about the manubrium.

As shown in FIG. 7B, the tapered locking head 226 provides a low profile for the locking head 226. In particular, the upper surface 276 curves toward the bone and tapers off so as to provide the lower profile and/or a smoother transition. Moreover, the curved lower surface 277 provides clearance for the strap 22 as the strap 22 extends into the slot 274. The lower profile and/or a smoother transition reduces the amount of irritation that may be caused to the surrounding tissue by the locking head 226. It should be appreciated that while the locking head 226 is positioned on an outer or top surface of the manubrium 228, the head 226 can be located proximate to other portions of the bone. For example, the locking head 226 could be positioned proximate to a side surface of the bone 18 as shown in FIG. 7C. It should also be appreciated, that the bone fixation member 14 and the bone fixation member 214 are interchangeable. That is the bone fixation member 14 can be placed about the manubrium 228 as desired, and the bone fixation member 214 can be placed about the bone segments 16a and 16b between ribs 35 as desired.

Figure 8:
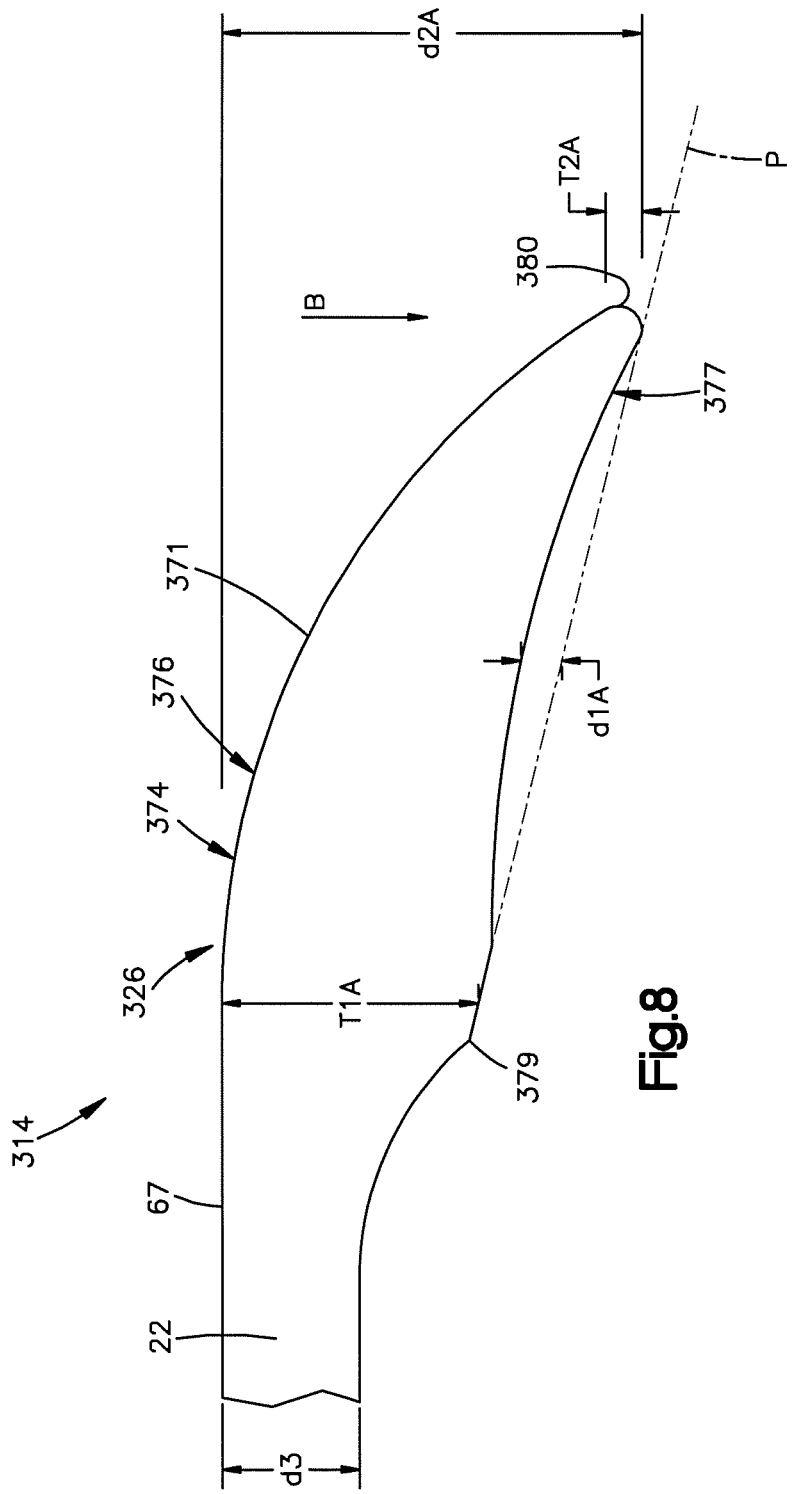
FIG. 8 is a side elevation view of a bone fixation member constructed in accordance with another embodiment, the bone fixation member having a locking head that is tapered so as to provide a lower profile and/or a smoother transition.

Now in reference to FIG. 8, a bone fixation member 314 can be configured to have a tapered locking head 326 so as to provide a lower profile and/or a smoother transition to thereby further reduce irritation that may be caused to the surrounding soft tissue by the locking head 326. The bone fixation member 314 is substantially similar to the bone fixation member 214 and includes like features unless otherwise described. Therefore, it should be appreciated that the bone fixation member 314 can include a strap 22, a leader portion 30, and a needle 34 as described with respect to the bone fixation member 214 shown in FIGS. 6A-6B.

As shown, the locking head 326 includes a housing 370 that defines a first or upper end 371 and a second or lower end 372 that is spaced from the first end 371 along the transverse direction. The locking head further includes a strap receiving slot 374 that extends through the housing 370 from the lower end 372 to the upper end 371 along a second direction. The slot 374 can extend along the second direction which can be along the transverse direction T or a direction having a directional component that extends along the transverse direction T. The strap receiving slot 374 is configured to receive the distal strap end D of the strap 22 such that the strap 22 is configured to translate through the slot 374 uni-directionally along an insertion direction B which can be the second direction so as to define a loop about the target bone 18.

The first end 371 of the housing 370 defines an upper surface 376, and the second end 372 of the housing 370 defines a lower surface 377. The first housing further defines two opposed side surfaces 378 that merge into the upper and lower surfaces 376 and 377. As shown in FIG. 8, the housing 370 is tapered along the longitudinal direction L and includes a distal head end 379 and a proximal head end 380 spaced from the distal head end 379 along the longitudinal direction L. The housing 370 can be tapered such that the distal head end 379 of the housing 370 has a first height $T_{1A}$ measured along the transverse direction T and the proximal head end 280 has a second height $T_{2A}$ measured along the transverse direction T. The first height $T_{1A}$ can be about 4.5 mm. The height or thickness of the housing 270 tapers as the housing extends proximally. Therefore, the second height $T_{2A}$ is less than the first height $T_{1A}$. The thicker distal head end 379 provides stability and rigidity to the locking head 326 while the thinner proximal head end 380 provides a lower profile and/or a smoother transition for the locking head 326 when the locking head 226 has been placed about the target bone. It should be appreciated, however, that the housing 370 can have any first height $T_{1A}$ and any second height $T_{2A}$ as desired.

The upper surface 376 is convex along the longitudinal direction L and the lower surface 377 is concave along the longitudinal direction L. The convex upper surface 376 and the concave lower surface 377 converge toward each other as they extend from the distal head end 379 toward the proximal head end 380 along the longitudinal direction L. The convex upper surface 376 provides a smooth outer surface for the locking head 326 to reduce irritation to the surrounding tissue. The concave lower surface 377 provides clearance for the strap 22 when the strap 22 is translated through the strap receiving slot 374. The lower surface 377 defines a shallow curve such that a maximum distance $d_{1A}$ measured between the lower surface 377 and a plane P defined by the locking head 326 that extends linearly through or otherwise liner tangential to a distal end of the lower surface 377 and a proximal end of the lower surface 277 is between about 3 mm and about 5 mm. It should be appreciated, however, that the lower surface can have a deeper curve as desired, or even be void of a curve as desired.

With continued reference to FIG. 8, the upper surface 376 of the locking head 326 merges into the upper surface or end 67 of the strap 22 such that a substantially no portion of the upper surface 376 protrudes above the upper surface 67. Moreover, a maximum distance $d_{2A}$ measured along the second direction between the upper most portion of the first end 371 of the locking head 326 and a lower most portion of the second end 372 is no more than 2 times a maximum distance or height $d_3$ measured between the upper surface or end 67 and the bone contacting surface or end 66 of the strap 22 along the second direction. Therefore, the geometry of the locking head 326 provides a lower profile and/or a smoother transition for the locking head 326 when in use.

As with the locking head 226, the locking head 326 is constructed as a single monolithic unit. It should be appreciated, however, that the locking head 326 can include a cap that is placed over the housing 370 such that the cap defines the first end 371. Therefore, the cap can define the convex upper surface 376 of the locking head 326.

Now in reference to FIGS. 9A-9D, the bone fixation assembly 10 can further include a bone punch 400 that is configured to form holes in the bone segments 16a and 16b, for example in respective manubrium portions 228. One of the bone fixation members, such as the bone fixation member 214 can be configured to extend through the holes so that the bone fixation member 214 can compress the manubrium portions 228 together to an approximated position. It should be appreciated, however, that the bone punch 400 can be configured to form holes in any portion of the sternal portions 16a and 16b, and can be further configured to form holes in any anatomical structure as desired.

Figure 9A:
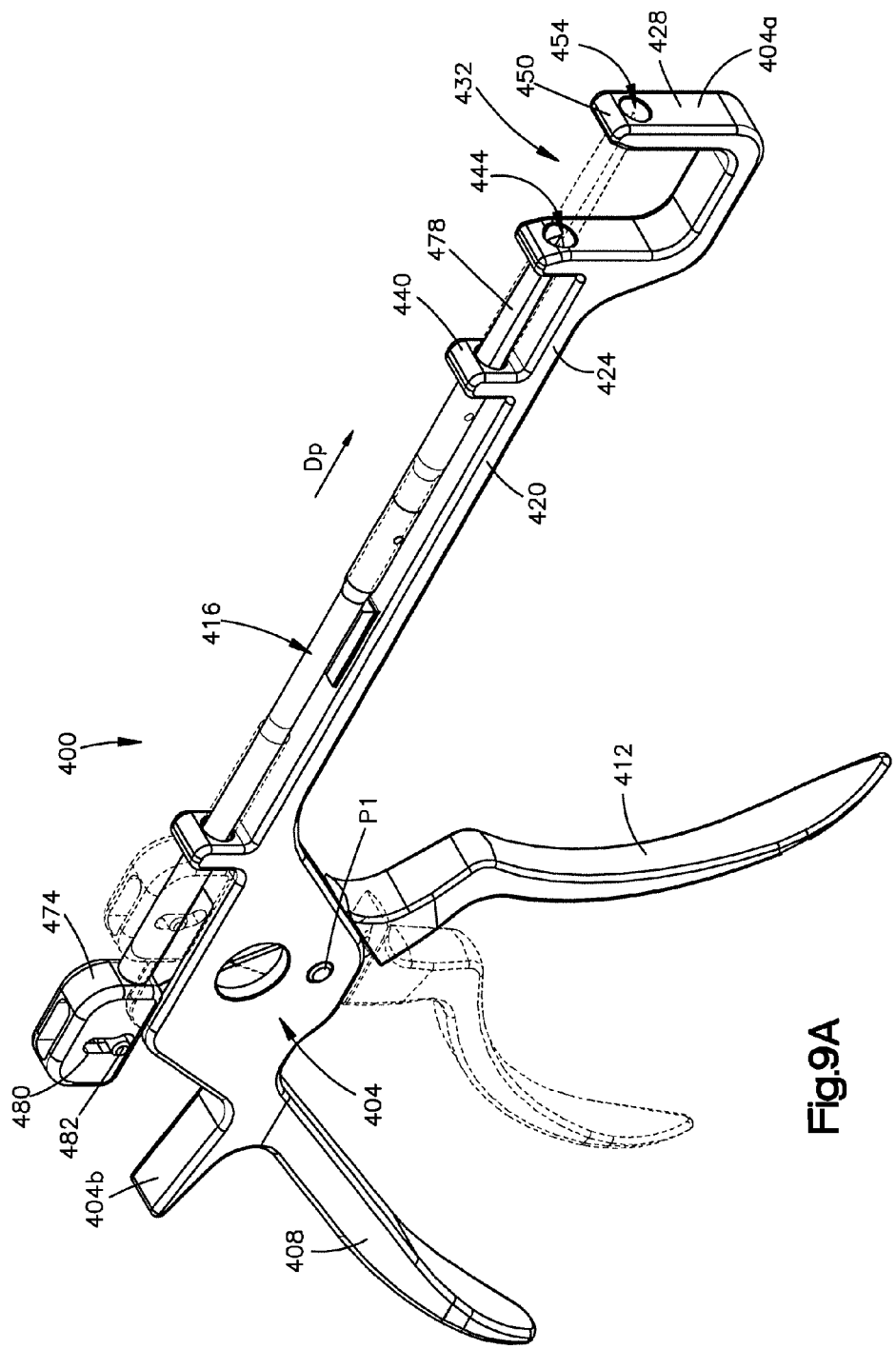
FIG. 9A is a perspective view of a bone punch constructed in accordance with an embodiment, the bone punch being configured to form a hole in a sternal bone such as the manubrium.
Figure 9B:
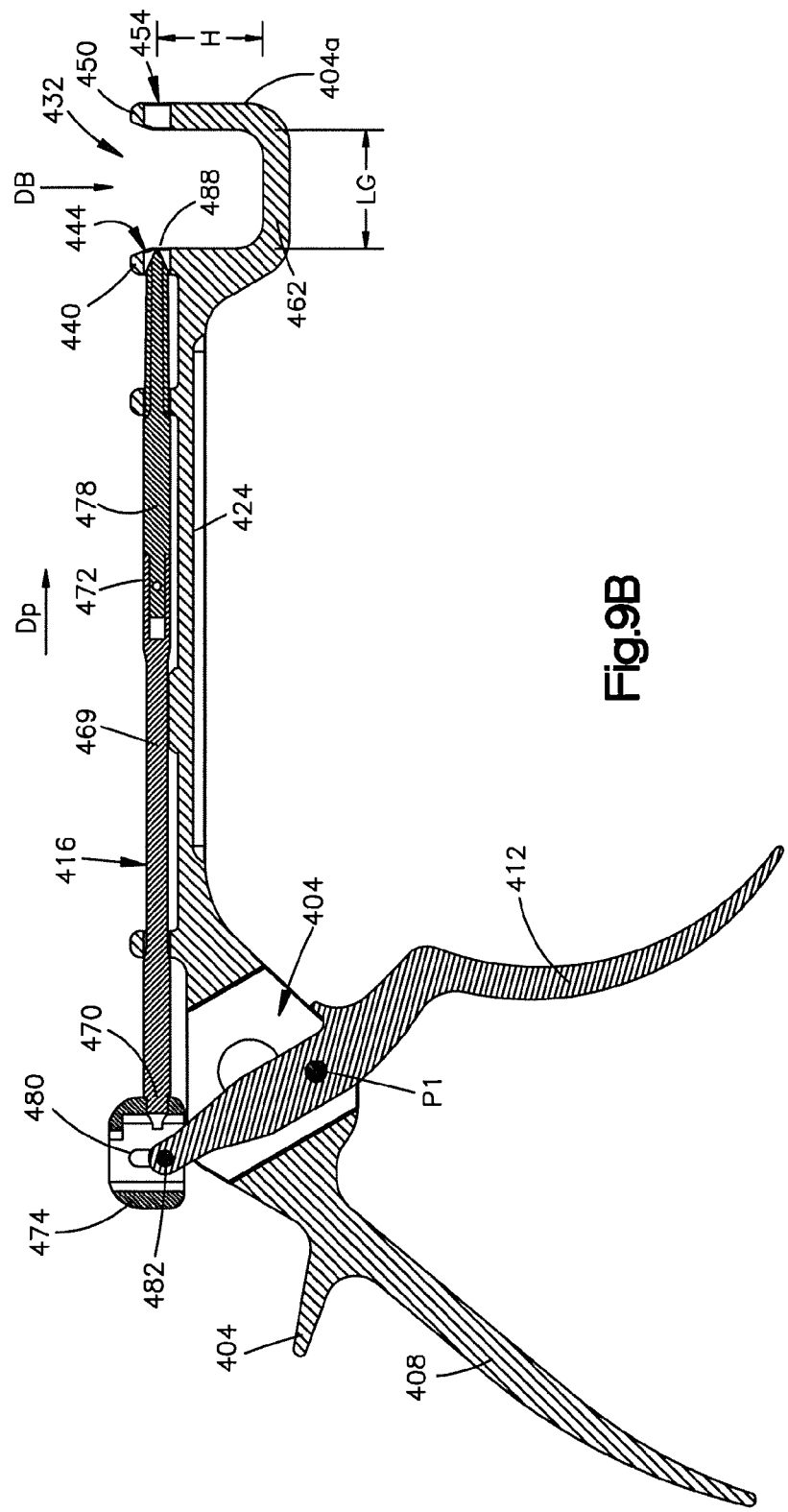
FIG. 9B is a side cross-sectional view of the bone punch shown in FIG. 9A.

As shown in FIGS. 9A and 9B, the bone punch 400 includes a body 404 that defines a front end 404a and an opposed rear end 404b, and a handle 408 that is supported by the body 404, and extends down from the body 404 proximate to the rear end 404b at an angle. The bone punch 400 further includes a trigger 412 that extends down from the body 404 at a location spaced forward from the handle 408 and a punch 416 that is translatably mounted to the body 404 and coupled to the trigger 412 such that actuation of the trigger 412 causes the punch 416 to translate along a punch direction $D_P$.

With continued reference to FIGS. 9A and 9B, the body 404 defines a boom arm 420 that is elongate along the punch direction $D_P$. The boom arm 420 defines a proximal punch housing 424 and a distal punch housing 428 that is spaced from the proximal punch housing 424 along the punch direction $D_P$ such that a bone receiving gap 432 is defined between the proximal and distal punch housings 424 and 428. The proximal punch housing 424 can include at least one support member 440, such as a plurality of support members 440 that support the punch 416. As shown in FIG. 9A each support member 440 defines an aperture 444 through which the punch 416 translates. The support members 440 are also configured to shield surrounding tissue from the moving punch 416. In the illustrated embodiment, the proximal punch housing 424 defines three support members 440, though it should be appreciated, that the proximal punch housing 424 can include any number of support members 440 or can be single housing that defines an elongate channel, as desired.

Similarly, the distal punch housing 428 can include a support member 450 that defines an aperture 454 that receives the punch 416 when the punch 416 has passed through the bone receiving gap 432. The support member 450 is configured to shield surround tissue from a tip of the punch 416. In some embodiments, the support member 450 can be configured to limit the translation of the punch 416. It should be appreciated, however, that the support member 450 can have any configuration as desired. For example, the support member 450 can define a recess rather than an aperture as illustrated.

The bone receiving gap 432 can be defined between a first support member 440a of the proximal punch housing 424 and the support member 450 of the distal punch housing 428 as illustrated. The bone receiving gap 432 can define a length $L_G$ measured along the punch direction $D_P$ that is sufficient to receive a target bone. For example, in the illustrated embodiment the length $L_G$ is sufficient for the bone receiving gap 432 to receive a manubrium portion 228. Therefore in the illustrated embodiment, the length $L_G$ can be between about 15 mm and about 30 mm and preferably about 22.5 mm. It should be appreciated, however, that the bone receiving gap 432 can be configured to receive any bone portion as desired and can therefore have any length $L_G$ as desired.

As shown in FIGS. 9A and 9B, the boom arm 420 further defines a bridge 462 that couples the proximal punch housing 424 to the distal punch housing 428. As shown in FIG. 9B, the bridge 462 can have a length that is substantially equal to the length $L_G$. The bridge 462 can define a stop surface 464 that is configured to abut the bone portion when the bone receiving gap 432 has fully received the bone portion. As shown in FIG. 9B, the bone receiving gap 432 can have a depth H measured along a bone receiving direction $D_B$ that is perpendicular to the punch direction $D_P$ from a central axis of the punch 416 to the stop surface 464. The depth H can be between 15 mm and 25 mm preferably about 20 mm. It should be appreciated, however, that the bone receiving gap 432 can have any depth H as desired.

With continued reference to FIGS. 9A and 9B, the punch 416 is translatably coupled to the body 404 such that the punch 416 is translatable along the punch direction $D_P$ between a first position whereby a tip of the punch 416 is proximal to the bone receiving gap 432 and a second position whereby the tip of the punch 416 extends into the support member 450 of the distal punch housing 428. The punch 416 can include a punch body 469 that is elongate along the punch direction $D_P$ and defines a proximal end 470 and a distal end 472 spaced from the proximal end 470 along the punch direction $D_P$. The punch 416 can further include a trigger housing 474 coupled to the proximal end 470 of the punch body 469 and a needle 478 coupled to the distal end 472 of the punch body 469. The needle 478 can be removably coupled to the punch body 469 so that the needle 478 can be replaceable.

The trigger housing 474 defines a slot 480 that is elongate along the bone receiving direction $D_B$. The trigger housing 474 can include a pin 482 that is slidable within the slot 480 and is configured to couple the trigger 412 to the trigger housing 474. As shown in FIG. 9B, the trigger 412 is rotatably coupled to the body 404 at a pivot $P_1$ and pivotally coupled to the trigger housing 474 by the pin 482. When the trigger 412 is squeezed or otherwise pivoted toward the handle 408 the trigger housing 474 is moved forward along the punch direction $D_P$. As the trigger housing 474 moves forward, the pin 482 moves within the slot 480 away from the body 404 so that the rotational motion of the trigger 412 is converted into translational motion of the punch 416.

As shown in FIGS. 9A and 9B, the needle 478 extends from the distal end of the punch body 469 and is elongate along the punch direction $D_P$. The needle 478 defines a bone engaging tip 488 at its distal or forward end. In the illustrated embodiment, the bone engaging tip 488 is pyramid shaped, though it should be appreciated, that the bone engaging tip 488 can have any configuration as desired. For example, the bone engaging tip 488 can be cone shaped. Further, the needle 478 can have any shape in cross-section as desired. For example, the needle 478 can be circular, polygonal, or oblong shaped as desired. The needle 478 is configured to move along the punch direction $D_P$ and through the bone receiving gap 432 when the punch 416 is translated from the first position to the second position. As shown in FIG. 9A, the bone engaging tip 488 is proximal to the bone receiving gap 432 when the punch is in the first position and is distal to the bone receiving gap 432 when the punch is in the second position. In the illustrated embodiment, the bone engaging tip 488 extends into the aperture 454 of the support member 450 when the punch 416 is in the second position. It should be appreciated, however, that the bone engaging tip 488 can stop short of the support member 450 when the punch 416 is in the second position as desired.

Now in reference to FIGS. 9C and 9D, the bone punch 400 can be configured to approach the bone segments 16a and 16b from an anterior approach. The bone punch 400 can be moved so that the bone receiving gap 432 extends into the fracture location 20. The bone punch 400 can then be rotated, such as rotated 90 degrees, so that the bone receiving gap 432 receives the target bone segment. It should be appreciated, however, that the bone punch 400 can be positioned in the fracture location 20 such that the bone receiving gap receives the bone segment by moving the bone punch 400 toward the target bone segment. In either, case it can be said that the bone receiving gap 432 receives the bone segment along the bone receiving direction $D_B$. As the bone receiving gap 432 is receiving the bone segment and after the bone receiving gap 432 has received the bone segment, the bone punch 400 is oriented such that the punch direction $D_P$ is substantially perpendicular to an anterior surface 498 of the bone segment. That is, the bone punch 400 is oriented such that at least a major directional component of the punch direction $D_P$ is perpendicular to the anterior surface 498 during positioning of the bone punch 400. Therefore, the bone punch 400 can be positioned such that the punch direction $D_P$ extends perpendicular form the anterior surface 498 or at a slight angle from the anterior surface 498. Once the bone punch 400 is in position, the trigger 412 can be actuated to thereby cause the needle 478 to move toward the second position and through the bone segment to thereby form a hole 499 in the bone segment. As shown in FIG. 9D, the needle 478 does not extend past the distal punch housing 428 when in the second position. By releasing the trigger 412, the needle 478 will return to the first position and the bone punch 400 can be removed from the target bone segment. The same steps can be performed on the other of the bone segments 16a and 16b to thereby form a hole in the other segment. Once the holes are formed, the bone fixation member can be passed through the holes and subsequently tightened so as to compress the bone segments in an approximated position.

Now in reference to FIGS. 10A-10D, a cap 500 that is separate from the locking head, can be configured to overlie and be coupled to the locking head 26 of the bone fixation element 14 to thereby transform the locking head 26 into a locking head that is similar to the locking head 226. Therefore, the cap 500 can be configured to remove sharp edges from and/or provide a low profile to the locking head 26 when coupled to the locking head 26. It should be appreciated, that while the cap 500 is described as being configured to overlie the locking head 26, the features of the cap 500 can be incorporated into caps that define the first ends 271 and 371 of the locking heads 226 and 326. That is, it can be said that the locking heads include a cap that is coupled to the housing such that the cap defines the first or upper surface of the locking head.

Figure 10B:
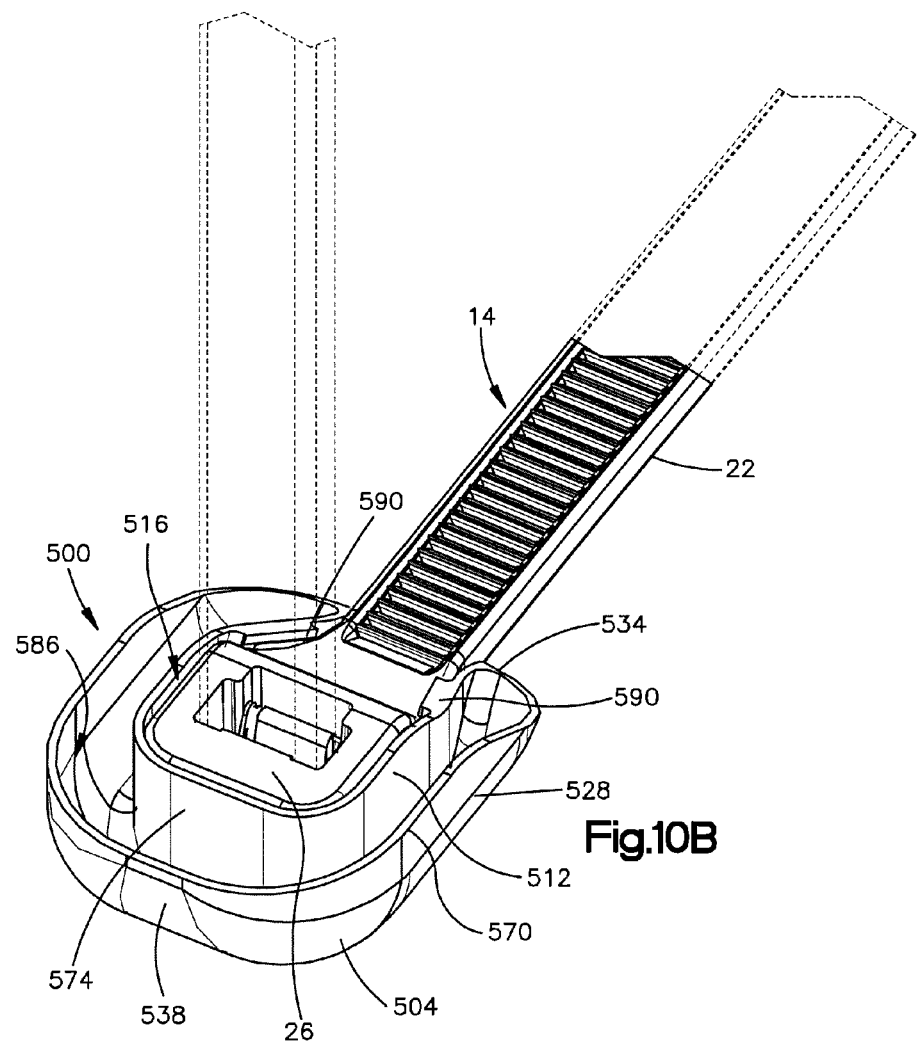
FIG. 10B is a bottom perspective view of the cap shown in FIG. 10A coupled to the locking head.
Figure 10C:
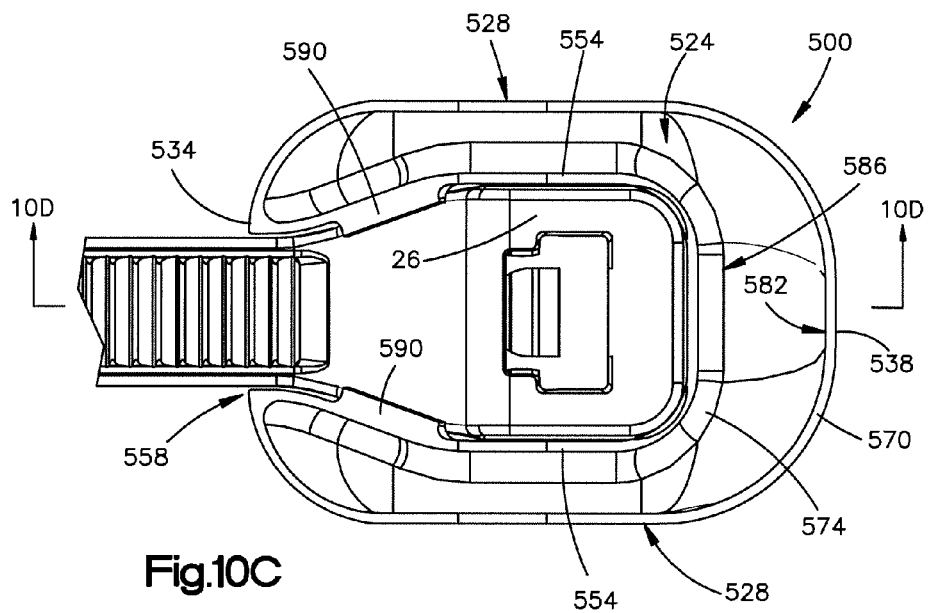
FIG. 10C is a bottom plan view of the cap shown in FIG. 10B coupled to the locking head.
Figure 10D:
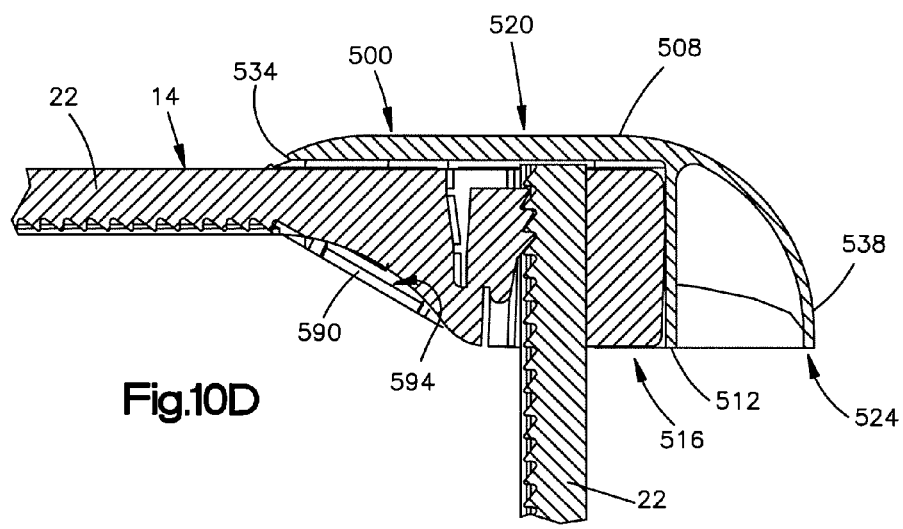
FIG. 10D is a cross-sectional view of the cap shown in FIG. 10C coupled to the locking head through the line 10D-10D.

As shown in FIGS. 10A and 10D the cap 500 includes a cap body 504 that is tapered so as to reduce irritation that may be caused to the surrounding soft tissue by the locking head 26 when the cap 500 is coupled to the locking head 26. The cap body 504 defines a first or upper end 508 and a second or lower end 512 that is spaced from the first end 508 along the transverse direction. The cap 500 further includes a cavity 516 that extends into the lower end 512. As shown in FIG. 10B, the cavity 516 is configured to receive at least a portion of, such as a major portion of the locking head 26. It should be appreciated, however, that the cavity 516 can be configured to receive any locking head or locking head housing as desired.

As shown in FIG. 10D, the first end 508 of the cap body 504 defines an upper surface 520 and the second end 512 of the cap body 504 defines a lower surface 524. The cap body 504 further defines two opposed side surfaces 528 that merge into the upper and lower surfaces 520 and 524. As shown, the cap body 504 is curved, or otherwise tapered along the longitudinal direction L and includes a distal body end 534 and a proximal body end 538 spaced from the distal body end 534 along the longitudinal direction L. The cap body 504 can be tapered from a location between the distal and proximal body ends 534 and 538 to the proximal body end 538. Therefore, the upper surface 520 is substantially convex along the longitudinal direction L. As shown in FIG. 10D, the upper surface 520 is curved such that the slope of the upper surface 520 increases as the upper surface 520 extends toward the proximal body end 538.

As shown in FIG. 10A, the lower surface 524 defines the cavity 516 such that the cavity 516 is defined by a ceiling 550 and opposed side walls 554. The distal end of the cap body 504 defines an opening 558 that extends into the cavity 516. The ceiling 550 and the side walls 554 are configured to cover the locking head 26 when the locking head 26 is received within the cavity 516, and the opening 558 is configured to allow the strap 22 to extend through the opening 558 when the locking head 26 is received within the cavity 516. The side walls 554 converge toward each other as they extend distally from the proximal body end 538 toward the distal body end 534 and terminate at the opening 558. Therefore, the distal ends of the ceiling 550 and side walls 554 define the opening 558 through which the strap 22 can extend.

Referring to FIG. 10C, the side surfaces 528 are also curved or otherwise tapered. Moreover, the side surfaces 528 are substantially convex and converge toward each other as they extend from a midline of the body 504 toward the distal body end 534 and toward the proximal body end 538 along the longitudinal direction L. Therefore, the body 504 generally has an oval shape as appeared from above the cap 500. The curved or otherwise tapered side surfaces 528 can reduce irritation that may be caused to the surrounding tissue by the locking head 26.

As shown in FIGS. 10A-10D, the cap body 504 can define an outer shell 570 and an inner shell 574 disposed within the outer shell 570. The outer shell 570 can define the upper surface 520 and the inner shell 574 can define the cavity 516. As shown in FIG. 10A, the outer shell 570 can define an inner surface 582 and the inner shell 574 can define an outer surface 586 that faces and is spaced apart from the inner surface 582 along at least a portion of the surfaces 582 and 586. Because the inner and outer surfaces 582 and 586 of the outer and inner shells 570 and 574, respectively, are spaced from each other, the inner shell 574 is configured to flex relative to the outer shell 570 as the cavity 516 receives the locking head 26. That is, the side walls 554 of the inner shell 574 are configured to flex outwardly as the cavity 516 receives the locking head 26. It should be appreciated, however, that the inner shell 574 can be configured to be non-flexible. Moreover, it should be appreciated, that the cap body 504 can be void of the inner shell 574 and can define an outer shell that defines the cavity 516.

With continued reference to FIGS. 10A-10D, the cap 500 can further include at least one, such as a pair of attachment members 590 that are configured to couple the cap 500 to the locking head 26. As shown, each attachment member 590 can extend inner from the cap body 504 such as from the inner shell 574. Each attachment member 590 can extend inward from a respective one of the side walls 554 into the cavity 516 from a location that is proximate to the lower end 512. The attachment members 590 can each define an abutment surface 594 that faces the ceiling 550 of the cavity 516 such that when the cap 500 is coupled to the locking head 26 the abutment surfaces 594 abut the second or lower end 71 of the locking head 26 to thereby secure the locking head within the cavity 516. It should be appreciated, that the attachment members can include other configurations. For example, the attachment members 590 can define C-clips. Moreover, it should be appreciated that the cap 500 can include features other than the attachment members 590 that are configured to couple the cap 500 to the locking head 26. For example, the cap 500 can be coupled to the locking head 26 with a frictional fit or with a fixation member such as a needle.

In operation, a bone fixation members 14 may be placed about the bone segments and of the sternum between adjacent ribs and the strap 22 can be pulled through the slot 74. As the strap 22 is translated through the slot 74 of the locking head 26 the locking teeth 42 and 82 can engage to prevent the tension that is induced in the strap 22 from causing the strap 22 to back out of the slot 74. Once the strap 22 has reached a maximum desired tension, the free end 124 of the bone fixation member 14 can be cut off. After the free end 124 is removed, the cap 500 can be coupled to the locking head 26 to thereby smooth out the sharp edges of the locking head 26. It should be appreciated, however, that the cap 500 can be configured to define a slot such that the cap 500 can be coupled to the locking head 26 prior to the strap 22 being inserted through the slot 74 of the locking head 26.

It should be appreciated that a bone fixation kit can be provided that includes at least one, such as a plurality of the bone fixation members 14, and/or at least one, such as a plurality of the bone fixation members 214 and/or at least one, such as a plurality of the bone fixation members 314, and/or at least one, such as a plurality of caps 500. The bone fixation kit can also include a bone fixation instrument 110 that is configured to tighten and then subsequently trim or otherwise cut the bone fixation members 14 and 214 and/or 314 and/or a bone punch 400 that is configured to form holes in the bone segments. It should be appreciated, however, that the bone fixation kit can include any combination of bone fixation members 14, bone fixation members 214, bone fixation members 314, caps 500, a bone fixation instrument 110, and a bone punch 400. For example, the bone fixation kit can include all bone fixation members 14, all bone fixation members 214, or some combination of bone fixation members 14 and bone fixation members 214 with or without the bone fixation instrument 110, with or without the bone punch, and with or without the caps 500.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:
1. A bone fixation kit comprising at least one bone fixation member that is configured to compress first and second bone segments in an approximated position, the at least one bone fixation member comprising:
   an elongate strap defining a distal end and a proximal end opposite the distal end, the elongate strap made of at least a first material and having a plurality of teeth, the elongate strap including a metal insert disposed at the distal end;
   a locking head that extends from the proximal end of the strap, the locking head having a housing, a strap receiving slot that extends through the housing, and a toothed locking member that extends into the strap receiving slot such that when the strap is inserted through the strap receiving slot in an insertion direction, the toothed locking member engages at least one of the teeth to prevent the strap from translating through the strap receiving slot in a direction that is opposite the insertion direction;
   a leader portion that extends from the distal end of the strap, wherein the leader portion is made of at least a second material that is different than the first material, such that the leader portion is more flexible than the strap; and
   a needle that extends from the leader portion such that the leader portion is connected between the strap and the needle.

2. The bone fixation kit of claim 1, wherein the strap defines a first length measured from the proximal end to the distal end, and the leader portion defines a second length that is at least 25% of the first length.

3. The bone fixation kit of claim 2, wherein the second length is between about 100 mm and about 300 mm.

4. The bone fixation kit of claim 1, wherein the leader portion has a diameter that is between about 0.6 mm and about 1.5 mm.

5. The bone fixation kit of claim 1, wherein the second material is stainless steel.

6. The bone fixation kit of claim 1, wherein the first material is PEEK or PEKK.

7. The bone fixation kit of claim 1, wherein the proximal end is spaced from the distal end in a first direction, the locking head defines a first end and a second end that is spaced from the first end in a direction that is perpendicular to the first direction, the first end being tapered in the first direction.

8. The bone fixation kit of claim 7, wherein a distance measured in the direction that is perpendicular to the first direction from an upper most portion of the first end to a lower most portion of the second end is no more than 1.5 times a thickness of the strap measured in the direction that is perpendicular to the first direction.

9. The bone fixation kit of claim 7, wherein the locking head includes a cap that defines the first end.

10. The bone fixation kit of claim 1, further comprising a cap that is separate from the locking head, the cap defining a cavity that is configured to receive at least a portion of the locking head so as to overlie at least a portion of the locking head.

11. The bone fixation kit of claim 10, wherein the cap includes a cap body that defines a distal body end and a proximal body end that is opposite the distal body end, the cap body further defining first and second ends that are spaced from each other in the insertion direction when the cap is coupled to the locking head, wherein the first end of the cap body is curved in a direction from a location between the distal body end and the proximal body end toward the proximal body end.

12. The bone fixation kit of claim 11, wherein the curved first end of the cap body is tapered.

13. The bone fixation kit of claim 11, wherein the cap body further includes an opening that extends through the distal body end and into the cavity, the opening configured to receive the strap when the cap is coupled to the locking head.

14. The bone fixation kit of claim 11, wherein the cap body defines an outer shell and an inner shell disposed within the outer shell, the inner shell defining the cavity.

15. The bone fixation kit of claim 14, wherein the outer shell defines an inner surface and the inner shell defines an outer surface that faces and is spaced apart from the inner surface such that the inner shell is configured to flex outwardly as the cavity receives the locking head.

16. The bone fixation kit of claim 10, wherein the cap further includes at least one attachment member that is configured to couple the cap to the locking head.

17. The bone fixation kit of claim 1, further comprising a bone punch configured to form a hole in at least one of the first and second bone segments.

18. The bone fixation kit of claim 17, wherein the first and second bone segments are first and second portions of a manubrium and the bone punch is configured to form a respective hole in each of the first and second portions from an anterior approach.

19. The bone fixation kit of claim 18, wherein the bone punch includes a boom arm that is elongate in a punch direction, the boom arm defining a proximal punch housing and a distal punch housing spaced from the proximal punch housing in the punch direction such that a bone receiving gap is defined between the proximal and distal punch housings, the bone punch further including a needle having a bone engaging tip, the needle being translatable in the punch direction between a first position whereby the tip is proximal to the bone receiving gap, and a second position whereby the needle extends through the bone receiving gap and toward the distal punch housing.

20. The bone fixation kit of claim 19, wherein the proximal punch housing includes a plurality of support members that house the needle such that the needle is translatable between the first and second positions.

21. The bone fixation kit of claim 20, wherein the tip extends into the distal punch housing when the needle is in the second position.

22. The bone fixation kit of claim 19, wherein the bone receiving gap is sized to receive the manubrium such that when the bone receiving gap has received the manubrium the punch direction is substantially perpendicular to an anterior surface of the manubrium.

23. The bone fixation kit of claim 19, wherein the bone engaging tip is pyramid shaped.

24. The bone fixation kit of claim 1, wherein the leader portion is coupled to the metal insert.

25. The bone fixation kit of claim 24, wherein the leader portion is coupled to the metal insert by a weld.

26. A bone fixation kit comprising at least one bone fixation member that is configured to compress first and second bone segments in an approximated position, the at least one bone fixation member comprising:
   an elongate strap defining a distal end and a proximal end opposite the distal end, the elongate strap made of at least a first material and having a plurality of teeth;
   a locking head that extends from the proximal end of the strap, the locking head having a housing, a strap receiving slot that extends through the housing, and a toothed locking member that extends into the strap receiving slot such that when the strap is inserted through the strap receiving slot in an insertion direction, the toothed locking member engages at least one of the teeth to prevent the strap from translating through the strap receiving slot in a direction that is opposite the insertion direction;
   a leader portion that extends from the distal end of the strap, wherein the leader portion is made of at least a second material that is different than the first material, such that the leader portion is more flexible than the strap;
   a needle that extends from the leader portion such that the leader portion is connected between the strap and the needle; and
   a cap that is separate from the locking head, the cap defining a cavity that is configured to receive at least a portion of the locking head so as to overlie at least a portion of the locking head.

27. The bone fixation kit of claim 26, wherein the cap includes a cap body that defines a distal body end and a proximal body end that is opposite the distal body end, the cap body further defining first and second ends that are spaced from each other in the insertion direction when the cap is coupled to the locking head, wherein the first end of the cap body is curved in a direction from a location between the distal body end and the proximal body end toward the proximal body end.

28. The bone fixation kit of claim 27, wherein the curved first end of the cap body is tapered.

29. The bone fixation kit of claim 27, wherein the cap body further includes an opening that extends through the distal body end and into the cavity, the opening configured to receive the strap when the cap is coupled to the locking head.

30. The bone fixation kit of claim 27, wherein the cap body defines an outer shell and an inner shell disposed within the outer shell, the inner shell defining the cavity.

31. The bone fixation kit of claim 30, wherein the outer shell defines an inner surface and the inner shell defines an outer surface that faces and is spaced apart from the inner surface such that the inner shell is configured to flex outwardly as the cavity receives the locking head.

32. The bone fixation kit of claim 26, wherein the cap further includes at least one attachment member that is configured to couple the cap to the locking head.

33. The bone fixation kit of claim 26, wherein the strap defines a first length measured from the proximal end to the distal end, and the leader portion defines a second length that is at least 25% of the first length.

34. The bone fixation kit of claim 33, wherein the second length is between about 100 mm and about 300 mm.

35. The bone fixation kit of claim 26, wherein the leader portion has a diameter that is between about 0.6 mm and about 1.5 mm.

36. The bone fixation kit of claim 26 wherein the second material is stainless steel.

37. The bone fixation kit of claim 26, wherein the first material is PEEK or PEKK.

38. The bone fixation kit of claim 26, wherein the strap includes a metal insert disposed at the distal end of the strap, and the leader portion is coupled to the metal insert by a weld.

39. The bone fixation kit of claim 26, further comprising a bone punch configured to form a hole in at least one of the first and second bone segments.

40. The bone fixation kit of claim 39, wherein the first and second bone segments are first and second portions of a manubrium and the bone punch is configured to form a respective hole in each of the first and second portions from an anterior approach.

41. The bone fixation kit of claim 40, wherein the bone punch includes a boom arm that is elongate in a punch direction, the boom arm defining a proximal punch housing and a distal punch housing spaced from the proximal punch housing in the punch direction such that a bone receiving gap is defined between the proximal and distal punch housings, the bone punch further including a needle having a bone engaging tip, the needle being translatable in the punch direction between a first position whereby the tip is proximal to the bone receiving gap, and a second position whereby the needle extends through the bone receiving gap and toward the distal punch housing.

42. The bone fixation kit of claim 41, wherein the proximal punch housing includes a plurality of support members that house the needle such that the needle is translatable between the first and second positions.

43. The bone fixation kit of claim 42, wherein the tip extends into the distal punch housing when the needle is in the second position.

44. The bone fixation kit of claim 41, wherein the bone receiving gap is sized to receive the manubrium such that when the bone receiving gap has received the manubrium the punch direction is substantially perpendicular to an anterior surface of the manubrium.

45. The bone fixation kit of claim 41, wherein the bone engaging tip is pyramid shaped.

* * * * *